(12) United States Patent
Yatvin et al.

(10) Patent No.: US 7,423,010 B2
(45) Date of Patent: *Sep. 9, 2008

(54) NONPOROUS MICROPARTICLE-PRODRUG CONJUGATES FOR TREATMENT OF INFECTION

(75) Inventors: Milton Yatvin, Portland, OR (US); Michael Stowell, Fulbourn (GB); Vincent Gallicchio, Lexington, KY (US); Michael Meredith, Lake Oswego, OR (US)

(73) Assignee: Oregon Health & Science University, Portland, OR (US)

( * ) Notice: Subject to any disclaimer, the term of this patent is extended or adjusted under 35 U.S.C. 154(b) by 277 days.

This patent is subject to a terminal disclaimer.

(21) Appl. No.: 11/064,416

(22) Filed: Feb. 22, 2005

(65) Prior Publication Data

US 2006/0008461 A1    Jan. 12, 2006

Related U.S. Application Data

(60) Division of application No. 10/050,271, filed on Jan. 15, 2002, now Pat. No. 6,858,582, which is a division of application No. 09/573,497, filed on May 16, 2000, now Pat. No. 6,339,060, which is a continuation of application No. 09/060,011, filed on Apr. 14, 1998, now Pat. No. 6,063,759, which is a continuation of application No. 08/691,891, filed on Aug. 1, 1996, now Pat. No. 5,840,674, which is a continuation of application No. 08/441,770, filed on May 16, 1995, now Pat. No. 5,543,391, which is a continuation of application No. 08/246,941, filed on May 19, 1994, now Pat. No. 5,543,390.

(51) Int. Cl.
*A01N 38/18* (2006.01)
*A61K 9/127* (2006.01)
*A61K 47/00* (2006.01)
*C12N 5/08* (2006.01)
*C07K 17/00* (2006.01)

(52) U.S. Cl. ............................ 514/2; 424/450; 435/176; 435/178; 435/179; 435/180; 435/325; 435/366; 530/300; 530/329; 530/331; 530/811; 530/813; 530/814; 530/815

(58) Field of Classification Search ........................ None
See application file for complete search history.

(56) References Cited

U.S. PATENT DOCUMENTS

| | | | | |
|---|---|---|---|---|
| 4,780,455 | A | * | 10/1988 | Lieberman et al. ............. 514/77 |
| 4,793,986 | A | * | 12/1988 | Serino et al. ................ 424/1.53 |
| 4,847,240 | A | * | 7/1989 | Ryser et al. .................... 514/12 |
| 5,017,566 | A | | 5/1991 | Bodor |
| 5,023,252 | A | | 6/1991 | Hseih |
| 5,024,998 | A | | 6/1991 | Bodor |
| 5,039,794 | A | | 8/1991 | Wier |

(Continued)

FOREIGN PATENT DOCUMENTS

EP    077529    4/1983

(Continued)

OTHER PUBLICATIONS

Abbas et al., "Antigen Presentation and T Cell Antigen Recognition," *Cellular as J. Mol. Immunol.* (W.B. Saunders Co.; Philadelphia), pp. 116-136.

(Continued)

*Primary Examiner*—David M Naff
(74) *Attorney, Agent, or Firm*—Klarquist Sparkman, LLP

(57) ABSTRACT

This invention provides novel methods and reagents for specifically delivering biologically active compounds to phagocytic mammalian cells. The invention also relates to specific uptake of such biologically active compounds by phagocytic cells and delivery of such compounds to specific sites intracellularly. The invention specifically relates to methods of facilitating the entry of antiviral and antimicrobial drugs and other agents into phagocytic cells and for targeting such compounds to specific organelles within the cell. The invention specifically provides compositions of matter and pharmaceutical embodiments of such compositions comprising conjugates of such antimicrobial drugs and agents covalently linked to particulate carriers generally termed microparticles. In particular embodiments, the antimicrobial drug is covalently linked to a microparticle via a cleavable linker moiety that is non-specifically cleaved in a phagocytic cell. In additional embodiments, the biologically-active compound is provided in an inactive, prodrug form that is activated by a chemical or enzymatic activity specific for cells infected by a microorganism, particularly a pathological or disease-causing microorganism. Thus, the invention provides cell targeting of drugs wherein the targeted drug is only activated in cells infected with a particular microorganism. Alternative embodiments of such specific drug delivery compositions also contain polar lipid carrier molecules effective in achieving intracellular organelle targeting in infected phagocytic mammalian cells. Particular embodiments of such conjugates comprise antimicrobial drugs covalently linked both to a microparticle via a cleavable linker molecule and to a polar lipid compound, to facilitate targeting of such drugs to particular subcellular organelles within the cell. Also provided are porous microparticles impregnated with antiviral and antimicrobial drugs and agents wherein the surface or outside extent of the microparticle is covered with a degradable coating that is degraded within a phagocytic mammalian cell. Also provided are nonporous microparticles coated with an antiviral or antimicrobial drug and further coated wherein the surface or outside extent of the microparticle is covered with a degradable coating that is degraded within a phagocytic mammalian cell. Methods of inhibiting, attenuating, arresting, combating and overcoming microbial infection of phagocytic mammalian cells in vivo and in vitro are also provided.

18 Claims, 13 Drawing Sheets

U.S. PATENT DOCUMENTS

| | | | | |
|---|---|---|---|---|
| 5,053,394 | A | * | 10/1991 | Ellestad et al. ............ 530/391.9 |
| 5,112,863 | A | | 5/1992 | Hashimoto |
| 5,124,146 | A | | 6/1992 | Neuwelt |
| 5,149,794 | A | * | 9/1992 | Yatvin et al. ................ 536/26.8 |
| 5,153,179 | A | | 10/1992 | Eibl |
| 5,177,064 | A | | 1/1993 | Bodor |
| 5,254,342 | A | | 10/1993 | Shen |
| 5,256,641 | A | * | 10/1993 | Yatvin et al. .................... 514/2 |
| 5,258,453 | A | * | 11/1993 | Kopecek et al. ............ 525/54.1 |
| 5,270,312 | A | | 12/1993 | Glase |
| 5,284,876 | A | | 2/1994 | Shashoua |
| 5,389,623 | A | | 2/1995 | Bodor |
| 5,405,834 | A | | 4/1995 | Bundgaard |
| 5,413,996 | A | | 5/1995 | Bodor |
| 5,434,137 | A | | 7/1995 | Black |
| 5,442,043 | A | | 8/1995 | Fukata |
| 5,466,683 | A | | 11/1995 | Sterling |
| 5,525,727 | A | | 6/1996 | Bodor |
| 5,543,389 | A | * | 8/1996 | Yatvin et al. .................... 514/2 |
| 5,543,390 | A | * | 8/1996 | Yatvin et al. .................... 514/2 |
| 5,543,391 | A | * | 8/1996 | Yatvin et al. .................... 514/2 |
| 5,840,674 | A | * | 11/1998 | Yatvin et al. ................ 510/392 |
| 6,063,759 | A | * | 5/2000 | Yatvin et al. .................... 514/2 |
| 6,339,060 | B1 | * | 1/2002 | Yatvin et al. .................... 514/2 |
| 6,455,073 | B1 | * | 9/2002 | Meredith et al. ............ 424/490 |
| 6,676,972 | B2 | * | 1/2004 | Meredith et al. ............ 424/490 |
| 6,858,582 | B2 | * | 2/2005 | Yatvin et al. .................... 514/2 |

FOREIGN PATENT DOCUMENTS

| | | |
|---|---|---|
| EP | 109484 | 4/1983 |
| EP | 301223 | 12/1983 |
| EP | 203676 | 12/1986 |
| EP | 279887 | 8/1988 |
| EP | 350287 | 1/1990 |
| WO | WO 85 02342 | 6/1985 |
| WO | WO 89 00166 | 11/1989 |
| WO | WO 89 10348 | 11/1989 |
| WO | WO 89 11299 | 11/1989 |
| WO | WO 89 02909 | 1/1990 |
| WO | WO 90 00555 | 1/1990 |
| WO | WO 90 01002 | 9/1990 |
| WO | WO 90 10448 | 9/1990 |
| WO | WO 90 04087 | 2/1991 |
| WO | WO 91 01750 | 2/1991 |
| WO | WO 91 04014 | 4/1991 |
| WO | WO 91 04745 | 4/1991 |
| WO | WO 91 02691 | 10/1991 |
| WO | WO 91 14438 | 10/1991 |
| WO | WO 91 16024 | 10/1991 |
| WO | WO 91 16024 A | 10/1991 |
| WO | WO 91 19726 A | 12/1991 |
| WO | WO 94 01131 | 1/1994 |
| WO | WO 94 01138 | 1/1994 |
| WO | WO 94 02178 | 2/1994 |
| WO | WO 94 03424 | 2/1994 |
| WO | WO 94/03434 | 2/1994 |
| WO | WO 94 06450 | 3/1994 |
| WO | WO 94 25616 | 11/1994 |
| WO | WO 95 07092 | 3/1995 |
| WO | WO 95 22963 | 8/1995 |
| WO | WO 95 32002 | 11/1995 |
| WO | WO 96 00537 | 1/1996 |
| WO | WO 96 04001 | 2/1996 |
| WO | WO 96 22303 | 7/1996 |

OTHER PUBLICATIONS

Afzelius et al., *Biochim. Biophys. Acta 979:* 231-238 (1989).

Alvarez-Dominquez et al., "Role of Complement Component C1q in Phagocytosis of *Listeria monocytogenes* by Murine Macrophage-Like Cell Lines," *Infect. Immun.* 61:3664-3672 (1993).

Anderson et al., *J. Am. Chem. Soc. 85:* 3093 (1963).

Ashborn et al., "Anti-HIV Activity of CD4-*Pseudomonas* Exotoxin on Infected Primary Human Lympocytes and Monocyte/Macrophages," *J. Infect. Dis. 163:* 703-709 (1991).

Baer, *Can. J. Biochem. Phys. 34:* 288-304 (1955).

Bai and Amidon, "Structural Specificity of Mucosal-Cell Transport and Metabolism of Peptide Drugs: Implications for Oral Peptide Drug Delivery," *Pharm. Res. 9:* 969-978 (1992).

Bai et al., "Utilization of Peptide Carrier System to Improve Intestinal Absorption: Targeting Prolidase as a Prodrug-Converting Enzyme," *J. Pharm. Sci. 81:* 113-116 (1992).

Barlow et al., "Mast cells and T lymphocytes in chronic urticaria," *Clinical & Experimental Allergy 25:* 317-322 (1995).

Baroni et al., "Expression of HIV in Lymph Node Cells of LAS Patients: Immunohistology, In Situ Hybridization, and Identification of Target Cells," *Am. J. Pathol. 133:* 498-506 (1988).

Berdel et al., *Lipids 22:* 943-946 (1987).

Bickel et al., "Pharmacologic effects in vivo in brain by vector-mediated peptide drug delivery," *Proc. Natl. Acad. Sci. USA 90:* 2618-2622 (1993).

Blakey, "Drug Targeting with Monoclonal Antibodies," *Acta Oncol. 31:* 91-97 (1992).

Blight et al., "Detection of hepatitis C virus RNA by in situ hybridization," *Liver 12:* 286-289 (1992).

Blum et al., "Bloood clearance and organ deposition of intravenously administered colloidal particles: the effects of particle size, nature and shape," *Int. J. Pharm. 12:* 135-146 (1982).

Boehnlein et al., "Characterization of Esterase and Alcohol Dehydrogenase Activity in Skin. Metabolism of Retinyl Palmitate to Retinol (Vitamin A) During Percutaneous Absorption," *Pharmaceutical Research 11:* 1155-1159 (1994).

Boman et al., "Cell-free immunity in Cecropia: A model system for antibacterial proteins," *Eur. J. Biochem. 201:* 23-31 (1990).

Borissova et al., "Biodegradable Microspheres. 17. Lysosomal Degradation of Primaquine-Peptide Spacer Arms," *Journal of Pharmaceutical Sciences*, vol. 84, No. 2, Feb. 1995, pp. 256-262.

Bou-Gharios et al., "Expression of ectopeptidases in scleroderma," *Annals of Rheumatic Disease 54:* 111-116 (1995).

Brewster et al., "Improved Delivery through Biological Membranes XXXI: Solubilization and Stabilization of an Estradiol Chemical Delivery System by Modified β-Cyclodextrins," *J. Pharm. Sci. 77:* 981-985 (1985).

Bromberg et al., "Detection of *Borditella pertussis* Associated with the Alveolar Macrophages of Children with Human Immunodeficiency Virus Infection," *Infect. Immun. 59:* 4715-4719 (1991).

Brown & Silvius, *Biochim. Biophys. Acta 1023:* 341-351 (1990).

Brown et al., "Induction of Cell Surface Peptidase Acitivity: A Global Response to Cell Stress Correlated with Apoptosis," *J. Cellular Biochemistry 54:* 320-331 (1994).

Brynestad et al., *J. Virol. 64:*680-685 (1990).

Buchmeier and Heffron, "Induction of *Salmonella* Stress Proteins upon Infection of Macrophages," *Science 248:* 730-732 (1990).

Büyüktimkin et al., "Synthesis and Enhancing Effect of Dodecyl 2-(*N*,*N*-Dimethylamino)propionate on the Transepidermal Delivery of Indomethacin, Clonidine, and Hydrocortisone," *Pharmaceutical Research 10:* 1632-1637 (1993).

Chang, "*Leishmania donovani:* Promastigote-Macrophage Surface Interactions in Vitro," *Exp. Parisitol.* 48:175-189 (1979).

Clarke et al., "Detection of HIV-1 in human lung macrophages using the polymerase chaine reaction," *AIDS 4:* 1133-1136 (1990).

Comiskey & Heath, *Biochim. Biophys. Acta 1024:* 307-317 (1990).

Cordier et al., "In vivo Activation of Alveolar Macrophages in Ovine Lentivirus Infection," *Clin. Immunol. Immunopathol. 55:* 355-367 (1990).

Couveur and Puisieux,. "Nano- and microparticles for the delivery of polypeptides and proteins," *Adv. Drug Deliv. Rev. 10:* 141-162 (1993).

Dachun et al., "Localization and Quantification of the Nonspecific Esterase in Injured Skin for Timing of Wounds," *Forensic Science International 53:* 203-213 (1992).

De Magistris et al., "Antigen Analog-Major Histocompatibility Complexes Act As Antagonists of the T Cell Receptor," *Cell 68:* 625-634 (1992).
Debs et al., *Biochim. Biophys. Acta 901:* 183-190 (1987).
Deres et al., *Nature* 342:561-564 (1989).
Dreyer at al., *Proc. Natl. Acad. Sci. USA 86:* 9752-9756 (1989).
Duncan, "Drug-polymer conjugates: potential for improved chemotherapy," *Anticancer Drugs 3:* 175-210 (1992).
Elliott et al., "Naturally processed peptides," *Nature 348:* 195-197 (1990).
Embretson et al., "Massive covert infection of helper T lympohocytes and macrophages by HIV during the incubation period of AIDS," *Nature 362:* 359-361 (1993).
Falk et al., "Allele-specific motifs revealed by sequencing of self-peptides eluted from MHC molecules," *Nature 351:* 290-291 (1991).
Falk et al., "Cellular peptide composition governed by major histocompatibility complex class I molecules," *Nature 348:* 248-251 (1990).
Faulk et al., "Transferrin-Adriamycin Conjugates which Inhibit Tumor Cell Proliferation without Interaction with DNA Inhibit Plasma Membrane Oxidoreductase and Proton Release in K562 Cells," *Biochem. Int. 25:* 815-822 (1991).
Faustman et al., "Linkage of Faulty Major Histocompatibility Complex Class I to Autoimmune Diabetes," *Science 254:* 1756-1776 (1991).
Franssen et al., "Low Molecular Weight Proteins as Carrier for Renal Drug Targeting: Preparation of Drug-Protein Conjugates and Drug-Spacer Derivatives and Their Catabolism in Renal Cortex Homogenates and Lysosmal Lysates," *J. Med. Chem. 35:* 1246-1259 (1992).
Frehel et al., Intramacrophage Growth of *Mycobacterium avium* during Infection of Mice, *Infect. Immun. 59:* 2207-2214 (1991).
Friedman et al., "Uptake and Intracellular Survival of *Bordatella pertussis* in Human Macrophages," *Infect. Immun. 60:* 4578-4585 (1992).
Frisch et al., "Parameters affecting the immunogenicity of a liposome-associated synthetic hexapeptide antigen," *Eur. J. Immun. 21:* 185-193 (1991).
Gaspar et al., "Drug targeting with polyalkylcyanoacrylate nanoparticles: in vitro activity of primaquine-loaded nanoparticles against intracellular *Leishmania donovani*," *Ann. Trop. Med. Parasitol. 86:* 41-49 (1992).
Gendelman et al., "Slow, persistent replication of lentiviruses: Role of tissue macrophages and macrophage precursors in bone marrow," *Proc. Natl. Acad. Sci. USA 82:* 7086-7090 (1985).
Germain & Hendrix, "MHC class II structure, occupancy and surface expression determined by post-endoplasmic reticulum antigen binding," *Nature 353:* 134-139 (1991).
Groisman et al., "Resistance to host antimicrobial peptides is necessary for *Salmonella* virulence," *Proc. Natl. Acad. Sci. USA 89:* 11939-11943 (1992).
Guéry et al., "Selective Immunosuppression by Administration of Major Histocompatibility Complex (MHC) Class II-binding Peptides. I. Evidence for In Vivo MHC Blockade Preventing T Cell Activation," *J. Exp. Med. 175:* 1345-1352 (1992).
Halstead et al., "Dengue Viruses and Mononuclear Phagocytes: I. Infection Enhancement by Non-Neutralizing Antibody," *J. Exp. Med.* 146:201-217 (1977).
Hashimoto et al., *Biochim. Biophys. Acta 816:* 163-168(1985).
Hashimoto et al., *Biochim. Biophys. Acta 816:* 169-178 (1985).
Heath and Martin, *Chem. Phys. Lipids 40:* 347-358 (1986).
Heath et al., *Biochim.Biophys. Acta 862:* 72-80(1986).
Heath, *Methods in Enzymol. 149:* 111-119.
Heinrich et al., "In-vivo Release of a GnRH Agonist from a Slow-release Poly(lactide-glycolide) Copolymer Preparation: Comparison in Rat, Rabbit and Guniea-Pig," *J. Pharm. Pharmacol. 43:* 762-765 (1991).
Henrikus and Kampffmeyer, "Ester hydrolysis conjugation reactions in intact skin and skin homogenate, and by liver esterase of rabbits," *Xenobiotica 22:* 1357-1366 (1992).
Heymann et al., "Organophosphate Sensitive and Insensitive Carboxylesterases in Human Skin," *Chem. Biol. Interactions 87:* 217-226 (1993).

Hopp, "Immunogenicity of a Synthetic HBsAg Peptide: Enhancement by Conjugation to a Fatty Acid Carrier," *Mol. Immunol. 21:* 13-16 (1984).
Horwitz and Maxfield, "*Legionella pneumphila* Inhibits Acidification of its Phagosome in Human Monocytes," *J. Cell Biol. 99:* 1936-1943 (1984).
Horwitz, "Interactions between Macrophages and Legionella pneumophila," *Curr. Top. Microbiol. Immunol.* 181:265-282 (1992).
Horwitz, "The Legionnaires' Disease Bacterium (*Legionella pneumophila*) Inhibits Phagosome-Lysosome Fusion in Human Monocytes," *J. Exp. Med. 158:* 2108-2126 (1983).
Hostetler et al., *J. Biol. Chem. 265:* 6112-6117 (1990).
Hunter et al., "Vesicular Systems (Niosomes and Liposomes) for Delivery of Sodium Stibogluconate in Experimental Murine Visceral Leishmaniasis," *J. Pharm. Phamacol. 40:* 161-165 (1988).
Jacobson et al., *FEBS Lett. 225:* 97-102 (1987).
Jardetzky et al., "Identification of self peptides bound to purified HLA-B27," *Nature 353:* 326-329 (1991).
Jones and Hirsch, "The Interaction between *Toxoplasma gondii* and Mammalian Cells," *J. Exp. Med.,* 136:1173-1194 (1972).
Kanno et al., "Aleutian Mink Disease Parvovirus Infection of Mink Peritoneal Macrophages and Human Macrophage Cell Lines," *J. Virol.* 67:2075-2082.
Kanno et al., "Identification of Aleutian Mink Disease Parvovirus Transcripts in Macrophages of Infected Adult Mink," *J. Virol.* 66:5305-5312 (1992).
King et al., "In Vivo Selection of Lymphocyte-Tropic and Macrophage-Tropic Variants of Lymphocytic Chorimeningitis Virus during Persistent Infection," *J. Virol. 64:* 5611-5616 (1990).
Kinsky & Loeder, *Biochim. Biophys. Acta 921:* 96-103 (1987).
Kinsky et al., *Biochim. Biophys. Acta 885:* 129-135 (1986).
Kinsky et al., *Biochim. Biophys. Acta 917:* 211-218 (1987).
Kishimoto, *Chem. Phys. Lipids 15:* 33-36 (1975).
Koenig et al., "Detection of AIDS Virus in Macrophages in Brain Tissue from AIDS Patients with Encephalopathy," *Science 233:* 1089-1093 (1986).
Kondo et al., "Latent human herpesvirus 6 infection of human monocytes/macrophages," *J. Gen. Virol. 72:* 1401-1408 (1991).
Koval & Pagano, "Lipid Recycling between the Plasma Membrane and Intracellular Compartments: Transport and Metabolism of Fluorescent Sphingomyelin Analogues in Cultured Fibroblasts," *J. Cell Biol. 108:* 2169-2181 (1989).
Kratz et al., "Keratinocyte conditioned medium stimulates type IV collagenase synthesis in cultured human keratinocytes and fibroblasts," *Brit. J. Dermatology 133:* 842-846 (1995).
Kreeger, *The Scientist,* Sep. 16, 1996, p. 6.
Krowka et al., *J. Immunol. 144:* 2535-2540 (1990).
Kubota et al., "Metabolism and Degradation of Betamethasone 17-Valerate in Homogenized Living Skin Equivalent," *Dermatology 188:* 13-17 (1994).
Kung and Redemann, *Biochim. Biophys. Acta 862:* 435-439 (1986).
Lamont et al., "The use of Peptide Analogs with Improved Stability and MHC Binding Capacity to Inhibit Antigen Presentation In Vitro and In Vivo," *J. Immunol. 144:* 2493-2498 (1990).
Lanzavecchia et al., "Irreversible association of peptides with class II MHC molecules in living cells," *Nature 357:* 249-252 (1992).
Larsen et al., "Stability of ketoprofen-dextran ester prodrugs in homogenates of various segments of the pig GI tract," *Acta Pharm. Nord. 3:* 41-44 (1991).
Lee et al., "Antibacterial peptides from pig intestines: Isolation of a mamalian cecropin," *Proc. Natl. Acad. Sci. USA 86:* 9159-9162 (1989).
Lehrer et al., "Defensins: Endogenous Antibiotic Peptides of Animal Cells," *Cell 64:* 229-230 (1991).
Lin et al., "Preparation of Enteric-Coated Microspheres of myplasma hyopneumoniae vaccine with cellulose acetate; (ii) effect of temperature and ph on the stability and release behaviour of microspheres," *Journal of Microencapsulation,* vol. 8, No. 4: 537-545 (1991).
Lipozencic et al., "Langerhans cells in the immunopathology of contact allergic dermatitis," *Eur. J. Histochem 38:* 303-310 (1994).
Loughery et al., *J. Immunol. Methods 132:* 25-35 (1990).
MacDonald, *J. Biol. Chem. 265:* 13533-13539 (1990).

Maciejewski et al., "Infection of Mononucleated Phagocytes with Human Cytomegalovirus," *Virol. 195:* 327-336 (1993).
Matsura et al., *J. Chem. Soc. Chem. Comm. xx:* 451-459 (1976).
Mauel et al., "Quantitative Release of Live Micro-organisms from Infected Macrophages by Sodium Dodecyl Sulfate," *Nature New Biol.* 244:93-94 (1973).
Mauel, "Macrophage-Parasite Interactions in *Leishmania* Infections," *J. Leukocyte Biol. 47:* 187-193 (1990).
McEntee et al., "Rhesus monkey macrophages infected with simian immunodeficiency virus cause rapid lysis of CD4-bearing lymphocytes," *J. Gen. Virol. 72:* 317-324 (1991).
Meltzer and Gendelman, "Mononuclear Phagocytes as Targets, Tissue Reservoirs, and Immunoregulatory Cells in Human Immunodeficiency Virus Disease," *Curr. Topics Microbiol. Immunol. 181:* 239-263 (1992).
Menger et al., "Synthesis of a Lipid/Peptide/Drug Conjugate: N4-(Acylpeptidyl)- ARA-C," *Bioconjugate Chemistry 5:* 162-166 (1994).
Moehrle et al., "Aminopeptidase M and dipeptidyl peptidase IV activity in epithelial skin tumors: a histochemical study," *J. Cutaneous Pathology 22:* 241-247 (1995).
Mukhergee & Heidelberger, *Cancer Res. 22:* 815-822 (1962).
Murray et al., "Experimental Visceral Leishmaniasis: Production of Interleukin 2 and Interferon y, Tissue Immune Reaction, and Response to Treatment with Interleukin 2 and Interferon y," *J. Immunol. 138:* 2290-2296 (1987).
Narayan et al., "Lentivirus Induced Arthritis in Animals," *J. Rheumatol.* 32:25-32 (1992).
Negre et al., "Antileishmanial Drug Targeting through Glycosylated Polymers Specifically Internalized by Macrophage Membrane Lectins," *Antimicrob. Agents and Chemother. 36:* 2228-2232 (1992).
Neto et al., *Biochem. Biophys. Res. Commun. 171:* 458-464 (1990).
Neurath et al., *J. Gen. Virol.* 65:1009-1014 (1984).
Ng & Heath, *Biochim. Biophys. Acta 981:* 261-268 (1989).
Nogueira and Cohn, "*Trypanosoma cruzi:* Mechanisms of Entry and Intracellular Fate in Mammalian Cells," *J. Exp. Med.* 143:1402-1420 (1976).
Nothnagel, *Biochim. Biophys. Acta 980:* 209-219 (1989).
Pagano et al., *J. Biol. Chem. 258:* 2034-2040 (1983).
Panuska et al., "Productive Infection of Isolated Human Alveolar Macrophages by Respiratory Syncytial Virus," *J. Clin. Invest. 86:* 113-119 (1990).
Pardridge, "Opioid Peptide Drug Development: Transport of Opioid Chimeric Peptides through the Blood-Brain Barrier," *NIDA Res. Monograph 120:* 153-168 (1992).
Parham, "Transporters of delight," *Nature 348:* 674-675 (1990).
Paul and Anderson, *J. Am. Chem. Soc. 82:* 4596-4600 (1960).
Payne et al., "Phagocytosis of *Legionella pneumophila* is Mediated by Human Monocyte Complement Receptors," *J. Exp. Med. 166:* 1377-1389 (1987).
Rahman et al., *Life Sci. 31:* 2061-2071 (1982).
Remy et al., *J. Org. Chem. 27:* 2491-2500 (1962).
Rosenberg et al., *J. Neurochem. 48:* 865-875 (1987).
Rowlinson-Busza and Epenetos, "Targeted delivery of biologic and other antineoplastic agents," *Curr. Opin. Oncol. 4:* 1142-1148 (1992).
Rubinstein et al., "In Vitro Evaluation of Calcium Pectinate: A Potential Colon-Specific Drug Delivery Carrier," *Pharm. Res. 10:* 258-263 (1993).
Sadegh-Nasseri and Germain, "A role for peptide in determining MHC class II structure," *Nature 353:* 167-170 (1991).
Saffran et al., "A New Approach to the Oral Administration of Insulin and Other Peptide Drugs," *Science 233:* 1081-1084 (1986).
Salord et al., *Biochim. Biophys. Acta 886:* 64-75 (1986).
Schlessinger and Horwitz, "Phagocytosis of Leprosy Bacilli is Mediated by Complement Receptors CR1 and CR3 on Human Monocytes and Complement Component C3 in Serum," *J. Clin. Invest. 85:* 1304-1314 (1990).

Schmitt et al., "Multiplication of Human Immunodeficiency Virus in Primary Cultures of Human Kupffer Cells—Possible Role of Liver Macrophage Infection in the Physiopathology of AIDS," *Res. Virol. 141:* 143-152 (1990).
Schnorr et al., "MxA-Dependent Inhibition of Measles Virus Glycoprotein Synthesis in a Stably Transfected Human Monocytic Cell Line," *J. Virol 67:* 4760-4768 (1993).
Seifert et al., *Biochem. J.* 267:795-802 (1990).
Sellon et al., "Wild-Type Equine Infectious Anemia Virus Replicates in Vivo Predominantly in Tissue Macrophages, Not in Peripheral Blood Monocytes," *J. Virol. 66:* 5906-5913 (1992).
Senter et al., "Activation of Prodrugs by Antibody-Enzyme Conjugates," *in Immunobiology of Peptides and Proteins,* Vol. VI, pp. 97-105 (1991).
Shanley and Pesanti, "Murine Peritoneal Macrophages Support Murine Cytomegalovirus Replication," *Infect. Immunol. 41:* 1352-1359 (1983).
Shen et al., "Cis-Aconityl Spacer between Daunomycin and Macromolecular Carriers: A Model of pH Sensitive Linkage Releasing Drug from a Lysomotropic Conjugate," *Biochem. Biopys. Res. Commun.* 102:1048-1052 (1981).
Sierra-Honigman et al., "Borna disease virus in peripheral blood mononuclear and bone marrow cells of neonatally and chronically infected rats," *J. Neuroimmunol. 45:* 31-36 (1993).
Sintov et al., "Enzymatic cleavage of disaccharaide side groups in insoluble synthetic polymers: a new method for specific delivery of drugs to the colon," *Biomaterials 14:* 483-490 (1993).
SivaSai et al., "Effect of Recombinant Interferon Gamma Administration on Lesional Monocytes/Macrophages in Lepromatous Leprosy Patients," *Int. J. Leprosy & Other Mycobacterial Diseases 61:* 259-269 (1993).
Smith and Khorana, *J. Amer. Chem. Soc. 80:* 1141-1145 (1958).
Steim et al., *Biochem. Biophys. Res. Commun. 171:* 451-457 (1990).
Strellrecht-Broomhall, "Evidence for Immune-Mediated Destruction as Mechanism for LCMV-Induced Anemia in Persistently Infected Mice," *Viral Immunol. 4:* 269-280 (1991).
Sturgill-Koszycki et al., "Lack of Acidification in *Mycobacterium* Phagosomes Produced by Exclusion of the Vesicular Proton-ATPase," *Science 263:* 678-681 (1994).
Trouet et al., "A covalent linkage between daunorubicin and proteins that is stable in serum and reversable by lysosomal hydrolases, as required for a lysomotropic drug-carrier conjugate: In vitro and in vivo studies," *Proc. Natl. Acad. Sci. USA* 79:626-629 (1982).
van Wijk et al., *Biochim. Biophys. Acta 1084:* 307-310 (1991).
Vandenbark et al., *Nature* 341:841-844 (1989).
Verbloom et al., *Synthesis 1032:* 807-809 (1981).
Wada et al., "Salt Formation of Latic Acid Oligomers as Matrix for Sustained Release of Drugs," *J. Pharm. Pharmacol. 43:* 605-608 (1991).
Wiesmüller et al., "The antibody response in BALB/c mice to the *Plasmodium falciparum* circumsporozoite repetitive epitope covalently coupled to synthetic lipopeptide adjuvant," *Immun. 72:* 109-113 (1991).
Wyrick and Brownridge, "Growth of *Chlamydia psittaci* in Macrophages," *Infect. Immunol.* 19:1054-1060 (1978).
Yatvin et al., "Targeting Lipophilic Prodrugs to Brain, Lung, and Spleen," *Journal of Cellular Biochemistry,* vol. 0, No. 19A: 173 (1995).
Yatvin, "A Multi-Modality Approach for the Treatment of AIDS," *Select. Cancer. Therapeut. 7:* 23-28 (1991).
Zasloff, "Margainins, a class of antimicrobial peptides from *Xenopus* skin: Isolation, characterization of two active forms, and partial cDNA sequence of a precursor," *Proc. Natl. Acad. Sci USA 84:* 5449-5453 (1987).
Zhang and McCormick, "Uptake of N-(4'-pyridoxyl)amines and release of amines by renal cells: A model for transporter-enhanced delivery of bioactive compounds," *Proc. Natl. Acad. Sci. USA 88:* 10407-10410 (1991).

* cited by examiner

NONPOROUS MICROPARTICLE-PRODRUG CONJUGATES FOR TREATMENT OF INFECTION

This application is a divisional of U.S. Ser. No. 10/050,271, filed Jan. 15, 2002, now U.S. Pat. No. 6,858,582, which is a divisional of U.S. Ser. No. 09/573,497, filed May 16, 2000, now U.S. Pat. No. 6,339,060, which is a continuation of U.S. Ser. No. 09/060,011, filed Apr. 14, 1998, now U.S. Pat. No. 6,063,759, which is a continuation of U.S. Ser. No. 08/691,891, filed Aug. 1, 1996, now U.S. Pat. No. 5,840,674, which is a continuation of U.S. Ser. No. 08/441,770, filed May 16, 1995, now U.S. Pat. No. 5,543,391, which is a continuation of U.S. Ser. No. 08/246,941, now U.S. Pat. No. 5,543,390.

BACKGROUND OF THE INVENTION

This invention was made with government support under grant 1-R01-CA49416 by the National Institutes of Health. The government has certain rights in the invention.

1. Field of the Invention

This invention relates to methods of facilitating the entry of biologically-active compounds into phagocytic cells and for targeting such compounds to specific organelles within the cell. The invention specifically provides compositions of matter and pharmaceutical embodiments of such compositions comprising conjugates of such biologically-active compounds covalently linked to particulate carriers generally termed microparticles. Particular embodiments of such compositions include compositions wherein the biologically-active compounds are antiviral and antimicrobial drugs. In such compositions the microparticle is coated with an antiviral or antimicrobial drug, and then further coated with organic coating material that is the target of a microorganism-specific protein having enzymatic activity. Thus, the invention provides cell targeting of drugs wherein the targeted drug is only released in cells infected with a particular microorganism. Alternative embodiments of such specific drug delivery compositions also contain polar lipid carrier molecules. Particular embodiments of such conjugates comprise a coated microparticle wherein an antiviral or antimicrobial drug is covalently linked to a polar lipid covalently linked to a polar lipid compound and the particle further coated with a coating material, to facilitate targeting of such drugs to particular subcellular organelles within the cell.

2. Background of the Related Art

A major goal in the pharmacological arts has been the development of methods and compositions to facilitate the specific delivery of therapeutic and other agents to the appropriate cells and tissues that would benefit from such treatment, and the avoidance of the general physiological effects of the inappropriate delivery of such agents to other cells or tissues of the body. The most common example of the need for such specificity is in the field of antibiotic therapy, in which the amount of a variety of antibiotic, antiviral and antimicrobial agents that can be safely administered to a patient is limited by their cytotoxic and immunogenic effects.

It is also recognized in the medical arts that certain cells and subcellular organelles are the sites of pharmacological action of certain drugs or are involved in the biological response to certain stimuli. In particular, it is now recognized that certain cell types and subcellular organelles within such cell types are reservoirs for occult infection that evades normal immune surveillance and permits the persistence of chronic infections. Specific delivery of diagnostic or therapeutic compounds to such intracellular organelles is thus desirable to increase the specificity and effectiveness of such clinical diagnostic or therapeutic techniques.

A. Drug Targeting

It is desirable to increase the efficiency and specificity of administration of a therapeutic agent to the cells of the relevant tissues in a variety of pathological states. This is particularly important as relates to antiviral and antimicrobial drugs. These drugs typically have pleiotropic antibiotic and cytotoxic effects that damage or destroy uninfected cells as well as infected cells. Thus, an efficient delivery system which would enable the delivery of such drugs specifically to infected cells would increase the efficacy of treatment and reduce the associated "side effects" of such drug treatments, and also serve to reduce morbidity and mortality associated with clinical administration of such drugs.

Numerous methods for enhancing the cytotoxic activity and the specificity of antibiotic drug action have been proposed. One method, receptor targeting, involves linking the therapeutic agent to a ligand which has an affinity for a receptor expressed on the desired target cell surface. Using this approach, an antimicrobial agent or drug is intended to adhere to the target cell following formation of a ligand-receptor complex on the cell surface. Entry into the cell could then follow as the result of internalization of ligand-receptor complexes. Following internalization, the antimicrobial drug may then exert its therapeutic effects directly on the cell.

One limitation of the receptor targeting approach lies in the fact that there are only a finite number of receptors on the surface of target cells. It has been estimated that the maximum number of receptors on a cell is approximately one million (Darnell et al., 1986, *Molecular Cell Biology*, 2d ed., W. H. Freeman: New York, 1990). This estimate predicts that there may be a maximum one million drug-conjugated ligand-receptor complexes on any given cell. Since not all of the ligand-receptor complexes may be internalized, and any given ligand-receptor system may express many-fold fewer receptors on a given cell surface, the efficacy of intracellular drug delivery using this approach is uncertain. Other known intracellular ligand-receptor complexes (such as the steroid hormone receptor) express as few as ten thousand hormone molecules per cell. Id. Thus, the ligand-receptor approach is plagued by a number of biological limitations.

Other methods of delivering therapeutic agents at concentrations higher than those achievable through the receptor targeting process include the use of lipid conjugates that have selective affinities for specific biological membranes. These methods have met with little success. (see, for example, Remy et al., 1962, *J. Org. Chem.* 27: 2491-2500; Mukhergee & Heidelberger, 1962, *Cancer Res.* 22: 815-22; Brewster et al., 1985, *J. Pharm. Sci.* 77: 981-985).

Liposomes have also been used to attempt cell targeting. Rahman et al., 1982, *Life Sci.* 31: 2061-71 found that liposomes which contained galactolipid as part of the lipid appeared to have a higher affinity for parenchymal cells than liposomes which lacked galactolipid. To date, however, efficient or specific drug delivery has not been predictably achieved using drug-encapsulated liposomes. There remains a need for the development of cell-specific and organelle-specific targeting drug delivery systems.

B. Phagocytic Cell-Specific Targeting

Cell-specific targeting is also an important goal of antimicrobial therapy, particularly in the event that a specific cell type is a target of acute or chronic infection. Targeting in the case of infection of a specific cell type would be advantageous because it would allow administration of biologically-toxic compounds to an animal suffering from infection with a microbial pathogen, without the risk of non-specific toxicity to uninfected cells that would exist with nontargeted administration of the toxic compound. An additional advantage of such targeted antimicrobial therapy would be improved pharmacokinetics that would result from specific concentration of the antimicrobial agent to the sites of infection, i.e., the infected cells.

Phagocytic cells such as monocytes and macrophages are known to be specific targets for infection of certain pathogenic microorganisms.

Sturgill-Koszycki et al., 1994, *Science* 263: 678-681 disclose that the basis for lack of acidification of phagosomes in *M. avium* and *M. tuberculosis*-infected macrophages is exclusion of the vesicular proton-ATPase.

Sierra-Honigman et al., 1993, *J. Neuroiummunol.* 45: 31-36 disclose Borna disease virus infection of monocytic cells in bone marrow.

Maciejewski et al., 1993, *Virol.* 195: 327-336 disclose human cytomegalovirus infection of mononucleated phagocytes in vitro.

Alvarez-Dominguez et al., 1993, *Infect. Immun.* 61: 3664-3672 disclose the involvement of complement factor C1q in phagocytosis of *Listeria monocytogenes* by macrophages.

Kanno et al., 1993, *J. Virol.* 67: 2075-2082 disclose that Aleutian mink disease parvovirus replication depends on differentiation state of the infected macrophage.

Kanno et al., 1992, *J. Virol.* 66: 5305-5312 disclose that Aleutian mink disease parvovirus infects peritoneal macrophages in mink.

Narayan et al., 1992, *J. Rheumatol.* 32: 25-32 disclose arthritis in animals caused by infection of macrophage precursors with lentivirus, and activation of quiescent lentivirus infection upon differentiation of such precursor cells into terminally-differentiated macrophages.

Horwitz, 1992, *Curr. Top. Microbiol. Immunol.* 181: 265-282 disclose *Legionella pneumophila* infections of alveolar macrophages as the basis for Legionnaire's disease and Pontiac fever.

Sellon et al., 1992, *J. Virol.* 66: 5906-5913 disclose equine infectious anemia virus replicates in tissue macrophages in vivo.

Groisman et al., 1992, *Proc. Natl. Acad. Sci. USA* 89: 11939-11943 disclose that *S. typhimurium* survives inside infected macrophages by resistance to antibacterial peptides.

Friedman et al., 1992, *Infect. Immun.* 60: 4578-4585 disclose *Bordetella pertussis* infection of human macrophages.

Stellrecht-Broomhall, 1991, *Viral Immunol.* 4: 269-280 disclose that lymphocytic choriomeningitis virus infection of macrophages promotes severe anemia caused by macrophage phagocytosis of red blood cells.

Frehel et al., 1991, *Infect. Immun.* 59: 2207-2214 disclose infection of spleen and liver-specific inflammatory macrophages by *Mycobacterium avium*, the existence of the microbe in encapsulated phagosomes within the inflammatory macrophages and survival therein in phagolysosomes.

Bromberg et al., 1991, *Infect. Immun.* 59: 4715-4719 disclose intracellular infection of alveolar macrophages.

Mauel, 1990, *J. Leukocyte Biol.* 47: 187-193 disclose that *Leishmania* spp. are intracellular parasites in macrophages.

Buchmeier and Heffron, 1990, *Science* 248: 730-732 disclose that *Salmonella typhimurium* infection of macrophages induced bacterial stress proteins.

Panuska et al., 1990, *J. Clin. Invest.* 86: 113-119 disclose productive infection of alveolar macrophages by respiratory syncytial virus.

Cordier et al., 1990, *Clin. Immunol. Immunopathol.* 55: 355-367 disclose infection of alveolar macrophages by visna-maedi virus in chronic interstitial lung disease in sheep.

Schlessinger and Horwitz, 1990, *J. Clin. Invest.* 85: 1304-1314 disclose *Mycobacterium leprae* infection of macrophages.

Clarke et al., 1990, *AIDS* 4: 1133-1136 disclose human immunodeficiency virus infection of alveolar macrophages in lung.

Baroni et al., 1988, *Am. J. Pathol.* 133: 498-506 disclose human immunodeficiency virus infection of lymph nodes.

Payne et al, 1987, *J. Exp. Med.* 166: 1377-1389 disclose *Mycobacterium tuberculosis* infection of macrophages.

Murray et al., 1987, *J. Immunol.* 138: 2290-2296 disclose that liver Kupffer cells are the initial targets for *L. donovani* infection.

Koenig et al., 1986, *Science* 233: 1089-1093 disclose human immunodeficiency virus infection of macrophages in the central nervous system.

Horwitz and Maxfield, 1984, *J. Cell Biol.* 99: 1936-1943 disclose that *L. pneumophila* survives in infected phagocytic cells at least in part by inhibiting reduction of intraphagosomic hydrogen ion concentration (pH).

Shanley and Pesanti, 1983, *Infect. Immunol.* 41: 1352-1359 disclose cytomegalovirus infection of macrophages in murine cells.

Horwitz, 1983, *J. Exp. Med.* 158: 2108-2126 disclose that *L. pneumophila* is an obligate intracellular parasite that is phagocytized into a phagosome wherein fusion with lysosome is inhibited.

Chang, 1979, *Exp. Parisitol.* 48: 175-189 disclose *Leischmania donovani* infection of macrophages.

Wyrick and Brownridge, 1978, *Infect. Immunol.* 19: 1054-1060 disclose *Chlamydia psittaci* infection of macrophages.

Nogueira and Cohn, 1976, *J. Exp. Med.* 143: 1402-1420 disclose *Trypanosoma cruzi* infection of macrophages.

Jones and Hirsch, 1972, *J. Exp. Med.* 136: 1173-1194 disclose *Toxoplasma gondii* infection of macrophages.

Persistent infection of phagocytic cells has been reported in the prior art.

Embretson et al., 1993, *Nature* 362: 359-361 disclose covert infection of macrophages with HIV and dissemination of infected cells throughout the immune system early in the course of disease.

Schnorr et al., 1993, *J. Virol.* 67: 4760-4768 disclose measles virus persistent infection in vitro in a human monocytic cell line.

Meltzer and Gendelman, 1992, *Curr. Topics Microbiol. Immunol.* 181: 239-263 provide a review of HIV infection of tissue macrophages in brain, liver, lung, skin, lymph nodes, and bone marrow, and involvement of macrophage infection in AIDS pathology.

Blight et al., 1992, *Liver* 12: 286-289 disclose persistent infection of liver macrophages (Kuppfer cells) by hepatitis C virus.

McEntee et al., 1991, *J. gen. Virol.* 72: 317-324 disclose persistent infection of macrophages by HIV resulting in destruction of T lymphocytes by fusion with infected macrophages, and that the macrophages survive fusion to kill other T lymphocytes.

Kalter et al., 1991, *J. Immunol.* 146: 298-306 describe enhanced HIV replication in macrophage CSF treated monocytes.

Meltzer et al., 1990, *Immunol. Today* 11: xx-yy describes HIV infection of macrophages.

Kondo et al., 1991, *J. gen. Virol.* 72: 1401-1408 disclose herpes simplex virus 6 latent infection of monocytes activated by differentiation into macrophages.

King et al., 1990, *J. Virol.* 64: 5611-5616 disclose persistent infection of macrophages with lymphocytic choriomeningitis virus.

Schmitt et al., 1990, *Res. Virol.* 141: 143-152 disclose a role for HIV infection of Kupffer cells as reservoirs for HIV infection.

Gendelman et al., 1985, *Proc. Natl. Acad. Sci. USA* 82: 7086-7090 disclose lentiviral (visna-maedi) infection of bone marrow precursors of peripheral blood monocytes/macrophages that provide a reservoir of latently-infected cells.

Halstead et al., 1977, *J. Exp. Med.* 146: 201-217 disclose that macrophages are targets of persistent infection with dengue virus.

Mauel et al., 1973, *Nature New Biol.* 244: 93-94 disclose that lysis of infected macrophages with sodium dodecyl sulfate could release live microbes.

Attempts at drug targeting have been reported in the prior art.

Rubinstein et al., 1993, *Pharm. Res.* 10: 258-263 report colon targeting using calcium pectinate (CaPec)-conjugated drugs, based on degradation of CaPec by colon specific (i.e., microflora-specific) enzymes and a hydrophobic drug incorporated into the insoluble CaPec matrices.

Sintov et al., 1993, *Biomaterials* 14: 483-490 report colon-specific targeting using conjugation of drug to insoluble synthetic polymer using disaccharide cleaved by enzymes made by intestinal microflora, specifically, β-glycosidic linkages comprising dextran.

Franssen et al., 1992, *J. Med. Chem.* 35: 1246-1259 report renal cell/kidney drug targeting using low molecular weight proteins (LMWP) as carriers, using enzymatic/chemical hydrolysis of a spacer molecule linking the drug and LMWP carrier.

Bai et al., 1992, *J. Pharm. Sci.* 81: 113-116 report intestinal cell targeting using a peptide carrier-drug system wherein the conjugate is cleaved by an intestine-specific enzyme, prolidase.

Gaspar et al., 1992, *Ann. Trop. Med. Parasitol.* 86: 41-49 disclose primaquine-loaded polyisohexylcyanoacrylate nanoparticles used to target *Leschmania donovani* infected macrophage-like cells in vitro.

Pardridge, 1992, *NIDA Res. Monograph* 120: 153-168 report opioid-conjugated chimeric peptide carriers for targeting to brain across the blood-brain barrier.

Bai and Amidon, 1992, *Pharm. Res.* 9: 969-978 report peptide-drug conjugates for oral delivery and intestinal mucosal targeting of drugs.

Ashborn et al., 1991, *J. Infect. Dis.* 163: 703-709 disclose the use of CD4-conjugated *Pseudomonas aeruginosa* exotoxin A to kill HIV-infected macrophages.

Larsen et al., 1991, *Acta Pharm. Nord.* 3: 41-44 report enzyme-mediated release of drug from dextrin-drug conjugates by microflora-specific enzymes for colon targeting.

Faulk et al.,-1991, *Biochem. Int.* 25: 815-822 report adriamycin-transferrin conjugates for tumor cell growth inhibition in vitro.

Zhang and McCormick, 1991, *Proc. Natl. Acad. Sci. USA* 88: 10407-10410 report renal cell targeting using vitamin B6-drug conjugates.

Blum et al., 1982, *Int. J. Pharm.* 12: 135-146 report polystyrene microspheres for specific delivery of compounds to liver and lung.

Trouet et al., 1982, *Proc. Natl. Acad. Sci. USA* 79: 626-629 report that daunorubicin-conjugated to proteins were cleaved by lysosomal hydrolases in vivo and in vitro.

Shen et al., 1981, *Biochem. Biophys. Res. Commun.* 102: 1048-1052 report pH-labile N-cis-acontinyl spacer moieties.

Monoclonal antibodies have been used in the prior art for drug targeting.

Serino et al, U.S. Pat. No. 4,793,986, issued Dec. 27, 1988, provides platinum anticancer drugs conjugated to polysaccharide (dextrin) carrier for conjugation to monoclonal antibodies for tumor cell targeting.

Bickel et al., 1993, *Proc. Natl. Acad. Sci. USA* 90: 2618-2622 discloses the use of a chimeric protein vector for targeting across blood-brain barrier using anti-transferrin monoclonal antibody.

Rowlinson-Busza and Epenetos, 1992, *Curr. Opin. Oncol.* 4: 1142-1148 provides antitumor immunotargeting using toxin-antibody conjugates.

Blakey, 1992, *Acta Oncol.* 31: 91-97 provides a review of antitumor antibody targeting of antineoplastic drugs.

Senter et al., 1991, *in Immunobiology of Peptides and Proteins*, Vol. VI, pp. 97-105 discloses monoclonal antibodies linked to alkaline phosphatase or penicillin-V amidase to activate prodrugs specifically at site of antibody targeting, for therapeutic treatment of solid tumors.

Drug-carrier conjugates have been used in the prior art to provide time-release drug delivery agents, Couveur and Puisieux, 1993, *Adv. Drug Deliv. Rev.* 10: 141-162 provide a review of microcapsule (vesicular), microsphere (dispersed matrix) and microparticle (1-250 μm)-based drug delivery systems, based on degradation of particle with drug release, to provide time release of drugs, oral delivery via transit through the intestinal mucosa and delivery to Kupffer cells of liver.

Duncan, 1992, *Anticancer Drugs* 3: 175-210 provide a review of improved pharmicokinetic profile of in vivo drug release of anticancer drugs using drug-polymer conjugates.

Heinrich et al., 1991, *J. Pharm. Pharmacol.* 43: 762-765 disclose poly-lactide-glycolide polymers for slow release of gonadotropin releasing hormone agonists as injectable implants.

Wada et al. 1991, *J. Pharm. Pharmacol.* 43: 605-608 disclose sustained-release drug conjugates with lactic acid oligomers.

Specifically, polymer-conjugated drugs have been reported in the prior art, and attempts to adapt particulate conjugates have also been reported.

Ryser et al., U.S. Pat. No. 4,847,240, issued Jul. 11, 1989, provides cationic polymers for conjugation to compounds that are poorly transported into cells. Examples include the antineoplastic drug methotrexate conjugated with polylysine and other polycationic amino acids are the carriers.

Ellestad et al., U.S. Pat. No. 5,053,394, issued Oct. 1, 1991, provides carrier-drug conjugates of methyltrithiol antibacterial and antitumor agents with a spacer linked to a targeting molecule which is an antibody or fragment thereof, growth factors or steroids.

Kopecek et al., U.S. Pat. No. 5,258,453, issued Nov. 2, 1993, provides antitumor compositions comprising both an anticancer drug and a photoactivatable drug attached to a copolymeric carrier by functional groups labile in cellular lysosomes, optionally containing a targeting moiety that are monoclonal antibodies, hormones, etc.

Negre et al., 1992, *Antimicrob. Agents and Chemother.* 36: 2228-2232 disclose the use of neutral mannose-substituted polylysine conjugates with an anti-leischmanial drug (allopurinol riboside) to treat murine infected macrophages in vitro.

Yatvin, 1991, *Select. Cancer. Therapeut.* 7: 23-28 discusses the use of particulate carriers for drug targeting.

Hunter et al., 1988, *J. Pharm. Phamacol.* 40: 161-165 disclose liposome-mediated delivery of anti-leischmanial drugs to infected murine macrophages in vitro.

Saffran et al., 1986, *Science* 233: 1081-1084 disclose drug release from a particulate carrier in the gut resulting from degradation of the carrier by enzymes produced by intestinal microflora.

Targeting of specific dyes and localization of the components of certain pathological organisms to the Golgi apparatus has been reported in the prior art.

Lipsky & Pagano, 1985, *Science* 228: 745-747 describe Golgi-specific vital dyes.

Pagano & Sleight, 1985, *Science* 229: 1051-1057 describes lipid transport in mammalian cells.

Pagano et al., 1989, *J. Cell Biol.* 109: 2067-2079 describes localization of fluorescent ceramide derivatives to the Golgi apparatus.

Barklis & Yatvin, 1992, *Membrane Interactions of HIV*, Wiley-Liss: N.Y., pp. 215-236 describe membrane organization of HIV viral coat in infected mammalian cells.

SUMMARY OF THE INVENTION

The present invention is directed to an improved method for delivering biologically-active compounds to phagocytic cells and cellular organelles of such phagocytic cells in vivo and in vitro. This delivery system achieves such specific delivery of biologically-active compounds in inactive, prodrug form which are then specifically activated within a phagocytic cell, most preferably a phagocytic mammalian cell, infected with a microorganism, most preferably a pathological or disease-causing microorganism. In preferred embodiments, the inactive prodrugs of the invention are provided as conjugates between polar lipids and biologically-active compounds. In one preferred embodiment of the invention is provided a biologically-active compound in inactive, prodrug form that can be delivered to phagocytic cells through conjugating the compound with a microparticle via an cleavable linker moiety. Alternatively, specific delivery is achieved by impregnating a biologically-active compound in inactive, prodrug form into a porous microparticle which is then coated with a coating material. In an alternative embodiment, the delivery system comprises a nonporous microparticle wherein a biologically-active compound in inactive, prodrug form is made to coat the particle, and the particle is then further coated by a coating material. As used herein, these different embodiments of the microparticles of the invention are generically defined as "microparticle-conjugated" embodiments. In preferred embodiments of each aspect of the invention, the biologically-active compound in inactive, prodrug form is most preferably provided as a conjugate of the biologically-active compound with a polar lipid via a specific linker moiety that is specifically cleaved in a phagocytic cell, most preferably a phagocytic mammalian cell, infected with a microorganism, most preferably a pathological or disease-causing microorganism, wherein the inactivated prodrug form of the biologically-active compound is activated thereby.

In each case, non-specific release of the polar lipid-biologically-active compound conjugate is achieved by enzymatic or chemical release of the inactive, prodrug form of the biologically-active compound from the microparticle by cleavage of the cleavable linker moiety or the coating material in a phagocytic cells, followed by specific release of the biologically-active compound in particular phagocytic cells. In preferred embodiments, wherein the biologically-active compound in inactive, prodrug form is provided as a conjugate of the biologically-active compound with a polar lipid via a specific linker moiety, activation is specifically accomplished by chemical or enzymatic cleavage of a specific linker moiety between the biologically-active compound and the polar lipid. Most preferably, the biologically-active compound is inactive or has reduced activity in the form of a polar lipid conjugate, wherein the activity of the compound is restored or increased upon specific cleavage of the linker moiety in a particular phagocytic cell. In preferred embodiments, the specific linker moiety is enzymatically cleaved by an enzyme that is produced by a microorganism, most preferably a pathological or disease-causing microorganism or which is induced by infection by a microorganism, most preferably a pathological or disease-causing microorganism. In additional preferred embodiments, the specific linker moiety is chemically cleaved under physiological conditions that are specific for phagocytic cells infected with a microorganism, most preferably a pathological or disease-causing microorganism.

In addition, conjugation of the biologically-active compound with a polar lipid provides for targeting of the conjugate to specific subcellular organelles. This invention has the specific advantage of facilitating the delivery of such compounds to specific subcellular organelles via the polar lipid carrier, achieving effective intracellular concentrations of such compounds more efficiently and with more specificity than conventional delivery systems. Moreover, the targeted biologically-active compounds comprising the conjugates are specifically activated or their activity increased at the intracellular target by cleavage of the specific linker moiety and release of the biologically-active compound at the targeted intracellular site.

The specific delivery of biologically-active compounds to phagocytic cells, most preferably phagocytic mammalian cell, is achieved by the present invention by chemical or physical association of the inactive prodrug form of the biologically-active compounds with a microparticle. Specific intracellular accumulation and facilitated cell entry is mediated by the phagocytic uptake of microparticle-conjugated biologically active compounds by such cells. Preferred embodiments of phagocytic cellular targets include phagocytic hematopoietic cells, preferably macrophages and phagocytic neutrophils.

Particularly preferred targets of the microparticle-conjugated biologically active compounds of the invention are phagocytic cells, preferably macrophages and phagocytic neutrophils, and in particular such cells that are infected with any of a variety of microorganism, most preferably a pathological or disease-causing microorganism. For such cells, the embodiments of the microparticle-conjugated biologically active compounds of the invention are comprised of cleavable linker moieties whereby chemical or enzymatic cleavage of said linker moieties are non-specifically cleaved inside the cells, and in preferred embodiments, inside phagocytic cells, wherein specific activation of the inactive prodrug to the active form of the biologically-active compound is achieved specifically in infected cells. In preferred embodiments, the inactive prodrugs are provided as conjugates of the biologically-active compounds with a polar lipid moiety via a specific linker moiety, wherein the biologically-active compound is activated from the prodrug state in phagocytic cells infected with a microorganism, most preferably a pathological or disease-causing microorganism, via specific cleavage of the linker moiety forming the conjugate between the polar lipid and the biologically-active compound. This provides for the specific release of biologically-active compounds, such as antiviral and antimicrobial drugs, to such infected cells, preferably targeted to specific intracellular targets for more effective delivery of such drugs within an infected phagocytic cell. It is understood that all phagocytic cells will take up such antiviral and antimicrobial embodiments of the microparticle-conjugated biologically active compounds of the invention, and will cleave the cleavable linker so as to release the prodrug form of the biologically-active compound in all phagocytic cells. However, it is an advantageous feature of the microparticle-conjugated biologically active compounds of the invention that specific activation of the inactive prodrug form of the biologically-active compounds is achieved only in phagocytic cells infected with a microorganism, most preferably a pathological or disease-causing microorganism. Release of biologically-active forms of such antiviral and antimicrobial drugs is dependent on the presence of the infectious microorganism in the phagocytic cell, in preferred embodiments, by cleavage of the specific linker moiety comprising the polar lipid-biologically active compound conjugate.

In preferred embodiments of this aspect of the invention, the biologically active compounds of the invention linked to microparticles via the cleavable linker are covalently linked to a polar lipid moiety. Polar lipid moieties comprise one or a plurality of polar lipid molecules. Polar lipid conjugates of the invention are comprised of one or a plurality of polar lipid molecules covalently linked to a biologically-active compound via a specific linker moiety as described above. Such specific linker moieties are provided having two linker functional groups, wherein the linker has a first end and a second end and wherein the polar lipid moiety is attached to the first end of the linker through a first linker functional group and the biologically-active compound is attached to the second end of the linker through a second linker functional group. In these embodiments of the invention, the linker functional groups attached to the first end and second ends of the linker are characterized as "strong", with reference to the propensity of the covalent bonds between each end of the linker molecule to be broken. In preferred embodiments of this aspect of the invention, the propensity of the covalent bonds between each of the ends of the linker molecule is low, that is, the polar lipid/biologically active compound conjugate is stable under intracellular physiological conditions in the absence of a chemical or enzymatic moiety specific for cellular infection by a microorganism, most preferably a pathological or disease-causing microorganism. In these embodiments, the specific linker moiety allows the biologically-active compound to accumulate and act at an intracellular site after being released from the microparticle only after having been released from the intracellular targeting polar lipid moiety.

In a particular embodiment of this aspect of the invention, the specific linker moiety is a peptide of formula (amino acid)$_n$, wherein n is an integer between 2 and 100, preferably wherein the peptide comprises a polymer of one or more amino acids.

In other embodiments of the compositions of matter of the invention, the biologically-active compound of the invention has a first functional linker group, and a polar lipid moiety has a second functional linker group, and the compound is directly covalently linked to the polar lipid moiety by a chemical bond between the first and second functional linker groups. In such embodiments, either the biologically-active compound or the polar lipid moiety comprises yet another functional linker group which is directly covalently linked to the cleavable linker moiety of the invention, which in turn is covalently linked to the microparticle. In preferred embodiments, each of the functional linker groups is a hydroxyl group, a primary or secondary amino group, a phosphate group or substituted derivatives thereof or a carboxylic acid group. In particular, in such embodiments the polar lipid/biologically active compound conjugate is preferably specifically cleaved in infected phagocytic mammalian cells. In these embodiments, the biologically-active compound is an inactive, prodrug state when covalently linked to the polar lipid, which activity of the biologically active compound in restored or increased after the conjugate has been broken.

In the various aspects of the polar lipid conjugates of the invention, preferred polar lipids include but are not limited to acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid.

Preferred biologically active compounds comprising the polar lipid conjugates linked to the microparticles of the invention include antiviral and antimicrobial compounds, drugs, peptides, toxins and other antibiotic agents.

The invention also provides compositions of matter comprising a porous microparticle into which is impregnated an inactive, prodrug form of a biologically-active compound, the impregnated porous microparticle being further coated with a coating material. In this aspect of the invention, the coating material is non-specifically degraded by chemical or enzymatic means inside a cell, preferably a phagocytic mammalian cell, allowing the release of the in inactive, prodrug form of the compound from the microparticle. In preferred embodiments, the coating material is a substrate for a protein having an enzymatic activity found cells, preferably mammalian phagocytic cells. In additional preferred embodiments, the biologically-active compound in inactive, prodrug form is provided as a conjugate of the biologically-active compound with a polar lipid via a specific linker moiety. In such embodiments, activation of the inactive prodrug is specifically accomplished by chemical or enzymatic cleavage of a specific linker moiety between the biologically-active compound and the polar lipid. Most preferably, the biologically-active compound is inactive or has reduced activity in the form of a polar lipid conjugate, wherein the activity of the compound is restored or increased upon specific cleavage of the linker moiety in a particular phagocytic cell that is infected with a microorganism, preferably a pathological or disease-causing microorganism.

In preferred embodiments, specific release of the biologically-active compound in particular phagocytic cells that are infected with a microorganism, most preferably a pathological or disease-causing microorganism is achieved via specific cleavage of a specific linker moiety that forms the conjugate between the polar lipid and the biologically-active compound. In these preferred embodiments, cleavage of the specific linker moiety is achieved by chemical or enzymatic cleavage of the linker moiety between the biologically-active compound and the polar lipid. Preferably, the biologically-active compound is inactive or has reduced activity in the form of a polar lipid conjugate, wherein the activity of the compound is restored or increased upon specific cleavage of the linker moiety in a particular phagocytic cell. In preferred embodiments, the specific linker moiety is enzymatically cleaved by an enzyme that is produced by a microorganism, most preferably a pathological or disease-causing microorganism or which is induced by infection by a microorganism, most preferably a pathological or disease-causing microorganism. In additional preferred embodiments, the specific linker moiety is chemically cleaved under physiological conditions that are specific for phagocytic cells infected with a microorganism, most preferably a pathological or disease-causing microorganism.

Preferred biologically active compounds comprising the polar lipid conjugates used to impregnate such porous microparticles include antiviral and antimicrobial compounds, drugs, peptides, toxins and other antibiotic agents.

In these embodiments, the biologically active compounds of the invention impregnated within porous microparticles are covalently linked to a polar lipid moiety. Polar lipid moieties comprise one or a plurality of polar lipid molecules. Polar lipid conjugates of the invention are comprised of one or a plurality of polar lipid molecules covalently linked to a biologically-active compound via a specific linker moiety as described above. Such specific linker moieties are provided having two linker functional groups, wherein the linker has a first end and a second end and wherein the polar lipid moiety is attached to the first end of the linker through a first linker functional group and the biologically-active compound is attached to the second end of the linker through a second linker functional group. In these embodiments of the invention, the linker functional groups attached to the first end and second ends of the linker is characterized as "strong", with reference to the propensity of the covalent bonds between each end of the linker molecule to be broken. In these embodiments, the specific linker moiety allows the biologically-active compound to accumulate and act at an intracellular site after being released from the microparticle only after having been released from the intracellular targeting polar lipid moiety. In these embodiments, the propensity of the covalent bonds between each of the ends of the linker molecule is low, that is, the polar lipid/biologically active compound conjugate is stable under intracellular physiological conditions in the absence of a chemical or enzymatic moiety specific for cellular infection by a microorganism, most preferably a pathological or disease-causing microorganism.

In a particular embodiment of this aspect of the invention, the specific linker moiety is a peptide of formula (amino acid)$_n$, wherein n is an integer between 2 and 100, preferably wherein the peptide comprises a polymer of one or more amino acids.

In other embodiments of the compositions of matter of the invention, the biologically-active compound of the invention has a first functional linker group, and a polar lipid moiety has a second functional linker group, and the compound is directly covalently linked to the polar lipid moiety by a chemical bond between the first and second functional linker groups. In such embodiments, either the biologically-active compound or the polar lipid moiety comprises yet another functional linker group which is directly covalently linked to the cleavable linker moiety of the invention, which in turn is covalently linked to the microparticle. In preferred embodiments, each of the functional linker groups is a hydroxyl group, a primary or secondary amino group, a phosphate group or substituted derivatives thereof or a carboxylic acid group. In particular, in such embodiments the polar lipid/biologically active compound conjugate is preferably specifically cleaved in infected phagocytic mammalian cells, wherein the activity of the biologically active compound in restored or increased after the conjugate has been broken.

In the various aspects of the polar lipid conjugates of the invention, preferred polar lipids include but are not limited to acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid.

The invention also provides compositions of matter comprising a nonporous microparticle onto which is coated a an inactive, prodrug form of a biologically-active compound, the non-porous microparticle being further coated with a coating material. In this aspect of the invention, the coating material is non-specifically degraded inside a cell, preferably a phagocytic mammalian cell, allowing the release of the inactive, prodrug form of the compound from the microparticle. In preferred embodiments, the coating material is a substrate for a protein having an enzymatic activity found cells, preferably mammalian phagocytic cells. In additional preferred embodiments, the biologically-active compound in inactive, prodrug form is provided as a conjugate of the biologically-active compound with a polar lipid via a specific linker moiety. In such embodiments, activation of the inactive prodrug is specifically accomplished by chemical or enzymatic cleavage of a specific linker moiety between the biologically-active compound and the polar lipid. Most preferably, the biologically-active compound is inactive or has reduced activity in the form of a polar lipid conjugate, wherein the activity of the compound is restored or increased upon specific cleavage of the linker moiety in a particular phagocytic cell that is infected with a microorganism, preferably a pathological or disease-musing microorganism.

In preferred embodiments, specific release of the biologically-active compound in particular phagocytic cells that are infected with a microorganism, most preferably a pathological or disease-causing microorganism is achieved via specific cleavage of the linker moiety forming the conjugate between the polar lipid and the biologically-active compound. In preferred embodiments, cleavage of the specific linker moiety is achieved by chemical or enzymatic cleavage of the linker moiety between the biologically-active compound and the polar lipid. Preferably, the biologically-active compound is inactive or has reduced activity in the form of a polar lipid conjugate, wherein the activity of the compound is restored or increased upon specific cleavage of the linker moiety in a particular phagocytic cell. In preferred embodiments, the specific linker moiety is enzymatically cleaved by an enzyme that is produced by a microorganism, most preferably a pathological or disease-causing microorganism or which is induced by infection by a microorganism, most preferably a pathological or disease-causing microorganism. In additional preferred embodiments, the specific linker moiety is chemically cleaved under physiological conditions that are specific for phagocytic cells infected with a microorganism, most preferably a pathological or disease-causing microorganism.

In this aspect of the invention, the inactive, prodrug form of the biologically-active compound of the invention will be understood to dissolve from the surface of the microparticle upon enzymatic or chemical degradation of the coating material. Release of the biologically-active compound can be accomplished simply be mass action, i.e., whereby the compound dissolves from the surface of the nonporous microparticle into the surrounding cytoplasm within the cell.

Preferred biologically active compounds used to prepare the coated, non-porous microparticles of this aspect of the invention include antiviral and antimicrobial compounds, drugs, peptides, toxins and other antibiotic agents.

In preferred embodiments, the biologically active compounds of the invention coated onto nonporous microparticles are covalently linked to a polar lipid moiety. Polar lipid moieties comprise one or a plurality of polar lipid molecules. The polar lipid conjugates of the invention are comprised of one or a plurality of polar lipid molecules covalently linked to a biologically-active compound via a specific linker moiety as described above. Such specific linker moieties are provided having two linker functional groups, wherein the linker has a first end and a second end and wherein the polar lipid moiety is attached to the first end of the linker through a first linker functional group and the biologically-active compound is attached to the second end of the linker through a second linker functional group. In these embodiments of the invention, the linker functional groups attached to the first end and second ends of the linker is characterized as "strong", with reference to the propensity of the covalent bonds between each end of the linker molecule to be broken. In preferred embodiments of this aspect of the invention, the specific linker moiety allows the biologically-active compound to act at an intracellular site after being released from the microparticle only after having been released from the intracellular targeting polar lipid moiety. In these embodiments, the propensity of the covalent bonds between each of the ends of the linker molecule is low, that is, the polar lipid/biologically active compound conjugate is stable under intracellular physiological conditions in the absence of a chemical or enzymatic moiety specific for cellular infection by a microorganism, most preferably a pathological or disease-causing microorganism.

In a particular embodiment of this aspect of the invention, the specific linker moiety is a peptide of formula (amino acid)$_n$, wherein n is an integer between 2 and 100, preferably wherein the peptide comprises a polymer of one or more amino acids.

In other embodiments of the compositions of matter of the invention, the biologically-active compound of the invention has a first functional linker group, and a polar lipid moiety has a second functional linker group, and the compound is directly covalently linked to the polar lipid moiety by a chemical bond between the first and second functional linker groups. In such embodiments the polar lipid/biologically-active conjugate is the inactive, prodrug form of the biologically-active compound. Said conjugate is impregnated into porous microparticles or coats non-porous microparticles as described above. In preferred embodiments, each of the functional linker groups is a hydroxyl group, a primary or secondary amino group, a phosphate group or substituted derivatives thereof or a carboxylic acid group. In particular, in such embodiments the polar lipid/biologically active compound conjugate is preferably specifically cleaved in infected phagocytic mammalian cells. In these embodiments, the biologically-active compound is an inactive, prodrug state when covalently linked to the polar lipid, which activity of the biologically active compound in restored or increased after the conjugate has been broken.

In the various aspects of the polar lipid conjugates of the invention, preferred polar lipids include but are not limited to acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid.

The invention also provides compositions of matter comprising a biologically-active compound in an inactive, prodrug form, wherein the prodrug is linked to a microparticle via a cleavable linker moiety. The cleavable linker moieties of the invention comprise two linker functional groups, wherein the cleavable linker moiety has a first end and a second end. The microparticle is attached to the first end of the cleavable linker moiety through a first linker functional group and the inactive, prodrug form of the biologically-active compound is attached to the second end of the cleavable linker moiety through a second linker functional group. The cleavable linker moieties of the invention are non-specifically cleaved inside a cell, preferably a phagocytic mammalian cell. In this aspect of the microparticles of the invention, the biologically active compound is provided in a non-biologically active form, wherein the compound is not activated merely by release from the microparticle. Rather, in this aspect of the microparticles of the invention, the biologically-active compound is specifically activated in a cell, preferably a phagocytic mammalian cell, that is infected with a microorganism, most preferably a pathological or disease-causing microorganism. In preferred embodiments, the biologically active compound is specifically activated by an enzymatic activity produced by a microorganism, most preferably a pathological or disease-musing microorganism or which is induced by infection by a microorganism, most preferably a pathological or disease-causing microorganism. In additional preferred embodiments, the biologically active compound is specifically activated by a chemical reaction under physiological conditions that are specific for phagocytic cells infected with a microorganism, most preferably a pathological or disease-causing microorganism.

In this aspect of the invention are also provided embodiments wherein the biologically active compound is covalently linked to a polar lipid moiety. Polar lipid moieties comprise one or a plurality of polar lipid molecules. Polar lipid conjugates of the invention are comprised of one or a plurality of polar lipid molecules covalently linked to a biologically-active compound. In preferred embodiments, activation of the biologically active compound as described above is achieved by specific cleavage of a covalent bond between the biologically active compound and a polar lipid moiety, or by specific cleavage of a specific linker moiety that comprises the conjugate between the polar lipid and the biologically-active compound.

In preferred embodiments of the invention, the biologically-active compound is a peptide. In other preferred embodiments, the biologically-active compound is a drug, most preferably an antiviral or antimicrobial drug. Preferred polar lipids include but are not limited to acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid.

Additional preferred embodiments of the microparticle-conjugated biologically active compounds of the invention also comprise a specific linker moiety wherein activation of the biologically active compound is achieved by specific cleavage of the linker moiety in a cell, preferably a phagocytic cell, infected with a microorganism, most preferably a pathological or disease-causing microorganism.

In a particular embodiment of this aspect of the invention, the specific linker moiety is a peptide of formula (amino acid)$_n$, wherein n is an integer between 2 and 100, preferably wherein the peptide comprises a polymer of one or more amino acids.

In other embodiments of the compositions of matter of the invention, the biologically-active compound of the invention has a first functional linker group, and a polar lipid moiety has a second functional linker group, and the compound is directly covalently linked to the polar lipid moiety by a chemical bond between the first and second functional linker groups. In such embodiments, either the biologically-active compound or the polar lipid moiety comprises yet another functional linker group which is directly covalently linked to a non-specific cleavable linker moiety of the invention, which in turn is covalently linked to the microparticle. In preferred embodiments, each of the functional linker groups is a hydroxyl group, a primary or secondary amino group, a phosphate group or substituted derivatives thereof or a carboxylic acid group. In particular, in such embodiments the polar lipid/biologically active compound conjugate is preferably specifically cleaved in infected phagocytic mammalian cells. In these embodiments, the biologically-active compound is an inactive, prodrug state when covalently linked to the polar lipid, which activity of the biologically active compound in restored or increased after the conjugate has been broken.

In specific aspects of the invention provided herein are microparticles comprising a drug. In preferred embodiments, the drug is an antiviral or antimicrobial drug.

As disclosed herein, the invention comprehends a microparticle and a polar lipid/biologically-active compound conjugate, preferably comprising a drug, more preferably comprising an antiviral or antimicrobial drug, wherein the conjugate is further covalently linked to a microparticle, impregnated within a microparticle, or coating a microparticle, wherein the microparticles are specifically taken up by cells, preferably phagocytic mammalian cells, and wherein the conjugates of the invention are non-specifically released inside the cell. In preferred embodiments, the conjugates of the invention further comprise a specific linker moiety. The specific linker moiety of the conjugates of the invention preferably releases the drug from the lipid, targets the conjugate to a subcellular organelle, incorporate the drug into a viral envelope, or perform other functions to maximize the effectiveness of the drug, wherein the drug is in an inactive or reduced activity form until it is specifically released from the conjugate in a cell infected with a microorganism, most preferably a pathological or disease-causing microorganism. In other preferred embodiments, the biologically-active compound and the polar lipid are directly linked, preferably covalently linked, and the compound is restored from an inactive, prodrug form to the activity of the biologically-active compound by cleavage of the polar lipid from the biologically-active compound. In yet other preferred embodiments, the biologically-active compound is directly linked to the microparticle, or impregnated within the microparticle, or coats the microparticle, and is specifically restored from an inactive, prodrug form to the activity of the biologically-active compound in a phagocytic cell infected by a microorganism, most preferably a pathological or disease-causing microorganism.

It will be recognized that heterogenous preparations of said microparticles of the invention, comprising either different microparticles conjugated, impregnated or coated with different biologically-active compounds, or one particular species conjugated, impregnated or coated with different biologically-active compounds of the invention, explicitly fall within the scope of the invention disclosed and claimed herein. Said preparations will be understood to comprise a multiplicity of the biologically-active compounds of the invention, preferably provided in an inactive, prodrug form.

The microparticle-drug conjugates of this invention have numerous advantages. First, the drug-microparticle conjugates are specifically taken up by cells, particularly phagocytic mammalian cells. Also, drugs, preferably antiviral and antimicrobial drugs comprising the drug-microparticle conjugates of the invention, are linked to the microparticle by a cleavable linker moiety that is non-specifically cleaved upon entry into phagocytic cells. More importantly, the drugs, preferably antiviral and antimicrobial drugs, are also preferably conjugated with a polar lipid, most preferably via a specific linker moiety. In this form, the drugs have reduced or inhibited biological activity, which activity is restored upon chemical or enzymatic cleavage of the specific linker moiety in appropriate phagocytic cells, for example, phagocytic cells infected with a microorganisms, preferably a pathological or disease-causing microorganism. Third, the drug-polar lipid conjugates of the invention will promote the intracellular targeting of a variety of potentially useful antiviral or antimicrobial drugs at pharmicokinetic rates not currently attainable. In this aspect, the range of targeted subcellular organelles is not limited per se by, for example, any particular, limited biological properties of the subcellular organelle such as the number and type of specific receptor molecules expressed by the organelle. In contrast to traditional attempts to simply target drugs to specific cells, this method may target drugs to specific intracellular organelles and other intracellular compartments. Fourth, the compositions of matter of the invention incorporate polar lipid/drug conjugates comprising a variable specific linker region that may allow pharmacologically-relevant rates of drug release from polar lipid moieties to be engineered into the compositions of the invention, thereby increasing their clinical efficacy and usefulness. Thus, time-dependent drug release and specific drug release in cells expressing the appropriate degradative enzymes are uniquely available using the microparticle-drug-lipid conjugates of the invention. Fifth, the conjugates of the invention can be combined with other drug delivery approaches to further increase specificity and to take advantage of useful advances in the art. One example of antiviral therapy would involve incorporating the conjugates of the invention into the viral envelope, thereby directly modifying its lipid composition and influencing viral infectivity. Finally, the prodrug-microparticle conjugates of the invention specifically encompass prodrugs which are biologically inactive unless and until pathogen infection-specific chemical or enzymatic cleavage converts such prodrugs into an active drug form inside a phagocytic mammalian cell.

Thus, the invention also provides a method of killing a microorganism infecting a mammalian cell. This method comprises contacting an infected phagocytic, mammalian cells with the compositions of matter of the invention. The invention also provides a method for treating a microbial infection in a human wherein the infecting microbe is present inside a phagocytic cell in the human, the method comprising administering a therapeutically effective amount of the compositions of matter of the invention to the human in a pharmaceutically acceptable carrier. Thus, the invention also provides pharmaceutical compositions comprising the compositions of matter of the invention in a pharmaceutically acceptable carrier.

Thus, in a first aspect the invention provides compositions of matter for targeting biologically active compounds to phagocytic cells. In a second aspect, the invention provides compositions of matter and methods for the specific release of biologically active compounds inside phagocytic cells. The invention in yet a third aspect provides methods and compositions for intracellular delivery of targeted biologically active compounds to phagocytic cells. The invention also provides for organelle-specific intracellular targeting of biologically active compounds, specifically to phagolysosomes and other subcellular structures including but not limited to the endoplasmic reticulum, the Golgi apparatus, mitochondria and the nucleus. In this aspect of the invention are also provided compositions and methods for organelle specific intracellular targeting using polar lipid moiety-linked compounds. In each of these aspects is provided methods and compounds for introducing biologically active compounds into phagocytic mammalian cells wherein the unconjugated compound would not otherwise enter said phagocytic cell. In this aspect is included the introduction of said biologically active compounds in chemical embodiments that would not otherwise enter the cell, for example, as phosphorylated embodiments. In yet another aspect is provided methods and compositions for the specific coordinate targeting of more than one biologically active compound to a specific cell type, that is, phagocytic mammalian cells. In another aspect, the invention provides reagents and compositions for introduction and specific release of antiviral or antimicrobial drugs and other biologically-active compounds into cells infected by a pathological microorganism. In a final aspect, the invention provides methods and reagents for delayed, sustained or controlled intracellular release of biologically active compounds conjugated to a micropartricle, or impregnated within a coated, porous microparticle, or coated onto a nonporous microparticle, wherein the degradation of either the coating, the cleavable linker, the specific linker moiety, the micropartice or any of these activity control points provides said delayed, sustained or controlled intracellular release of the biologically active compound of the invention.

Specific preferred embodiments of the present invention will become evident from the following more detailed description of certain preferred embodiments and the claims.

DETAILED DESCRIPTION OF THE PREFERRED EMBODIMENTS

Figure 1:
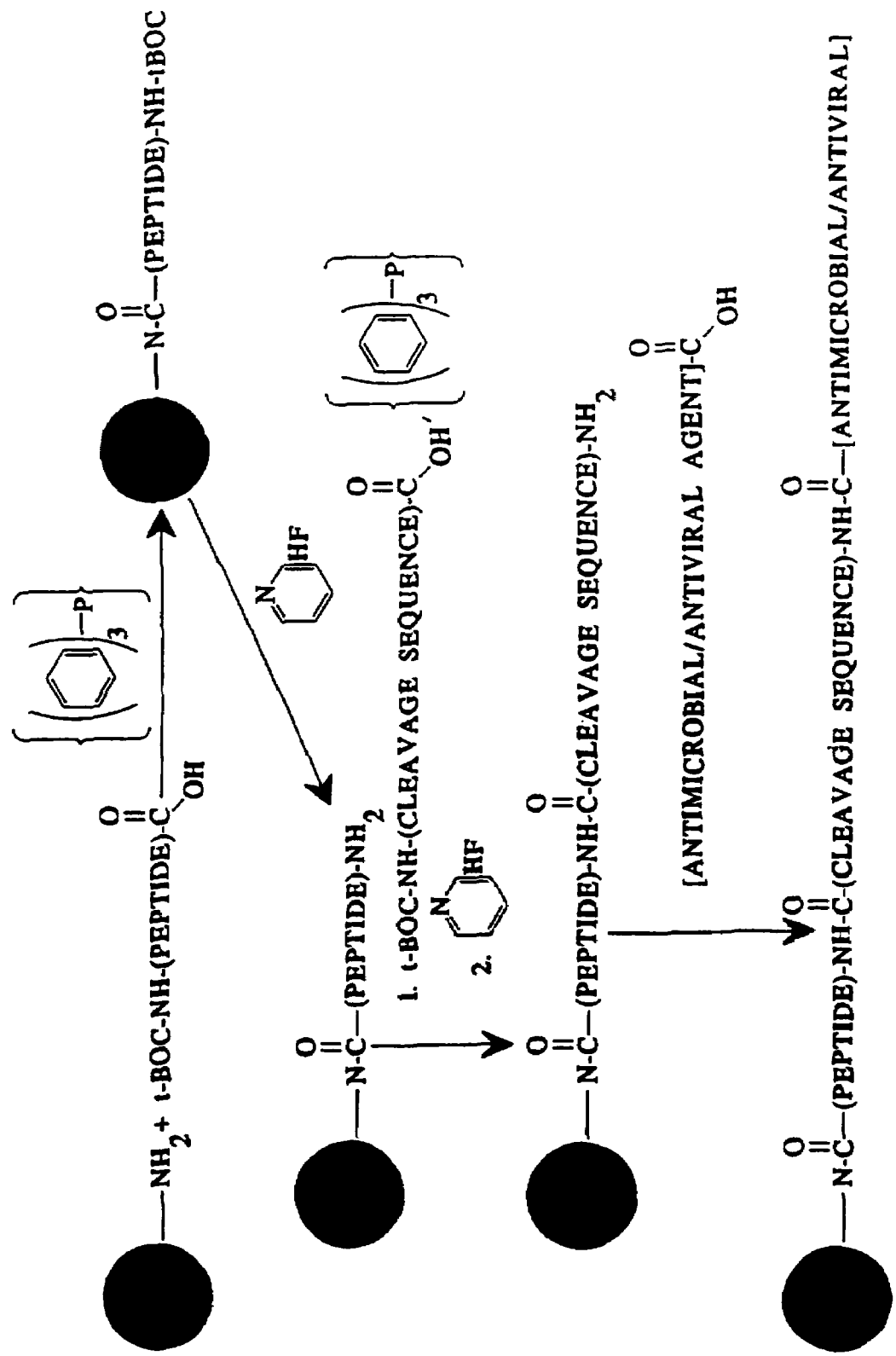
FIG. 1 depicts the synthetic scheme put forth in Example 1.
Figure 2:
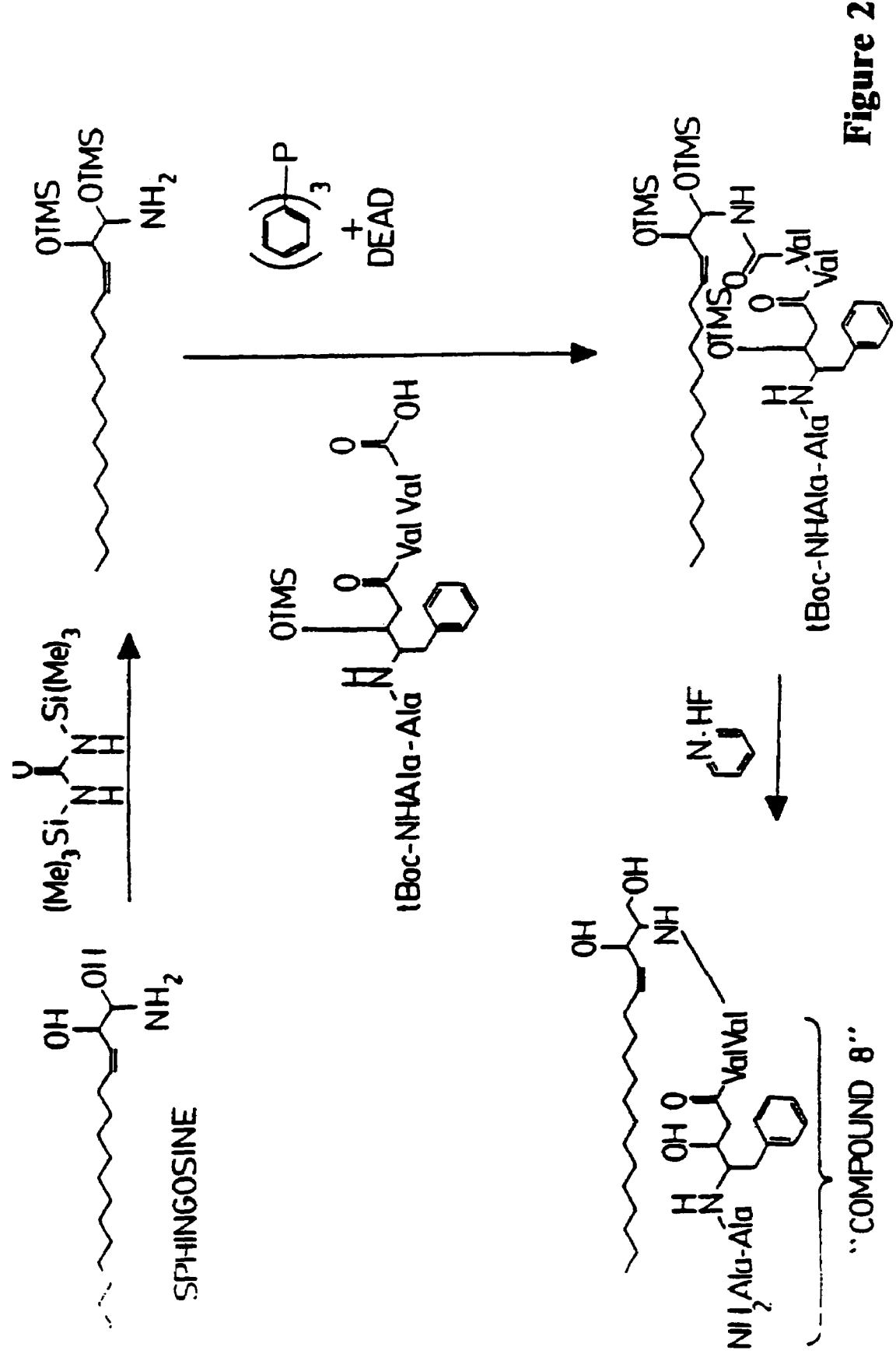
FIG. 2 depicts the synthetic scheme put forth in Example 2.
Figure 3A:
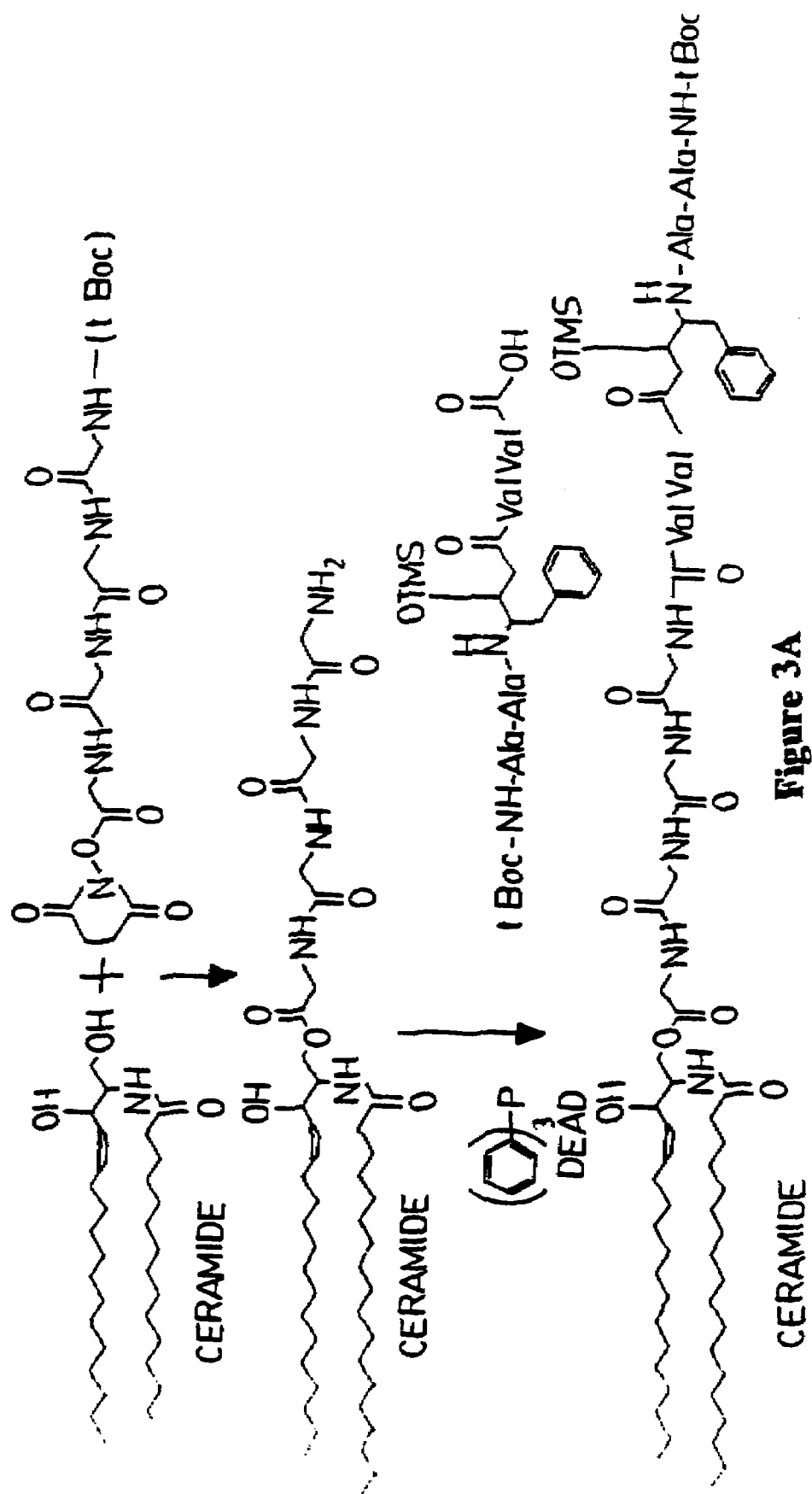
FIG. 3 depicts the synthetic scheme put forth in Example 3.
Figure 3B:
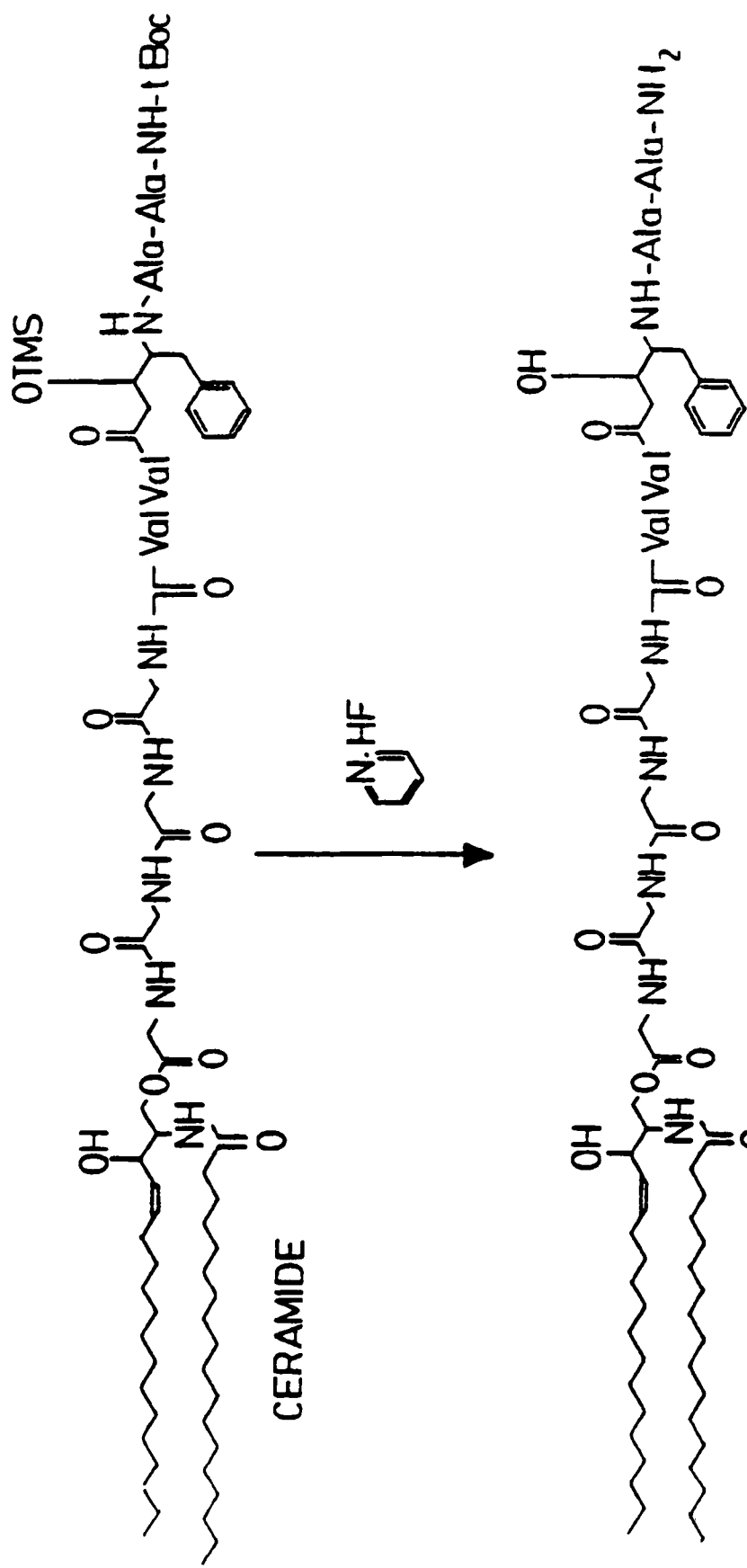
Figure 4:
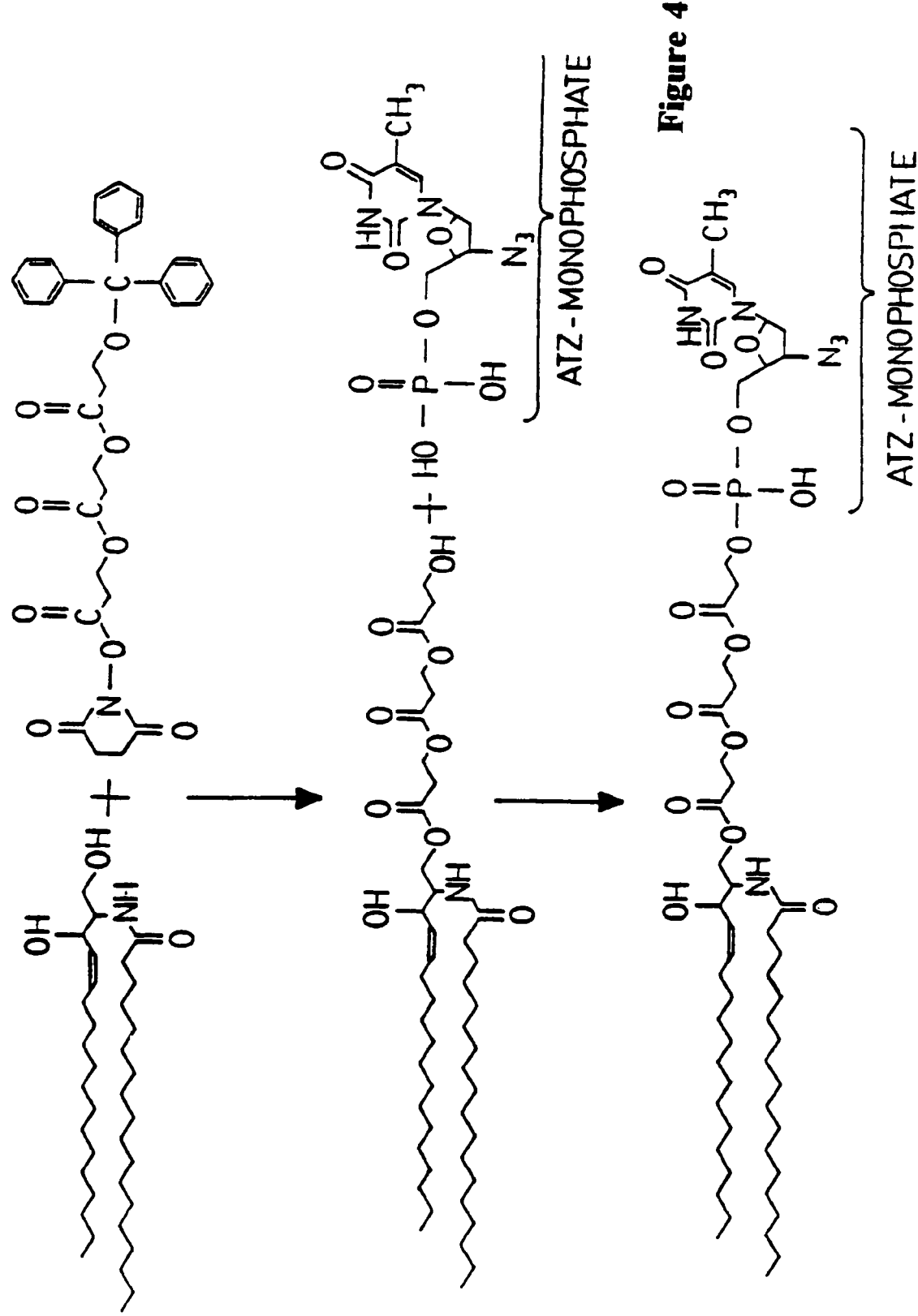
FIG. 4 depicts the synthetic scheme put forth in Example 4.
Figure 5:
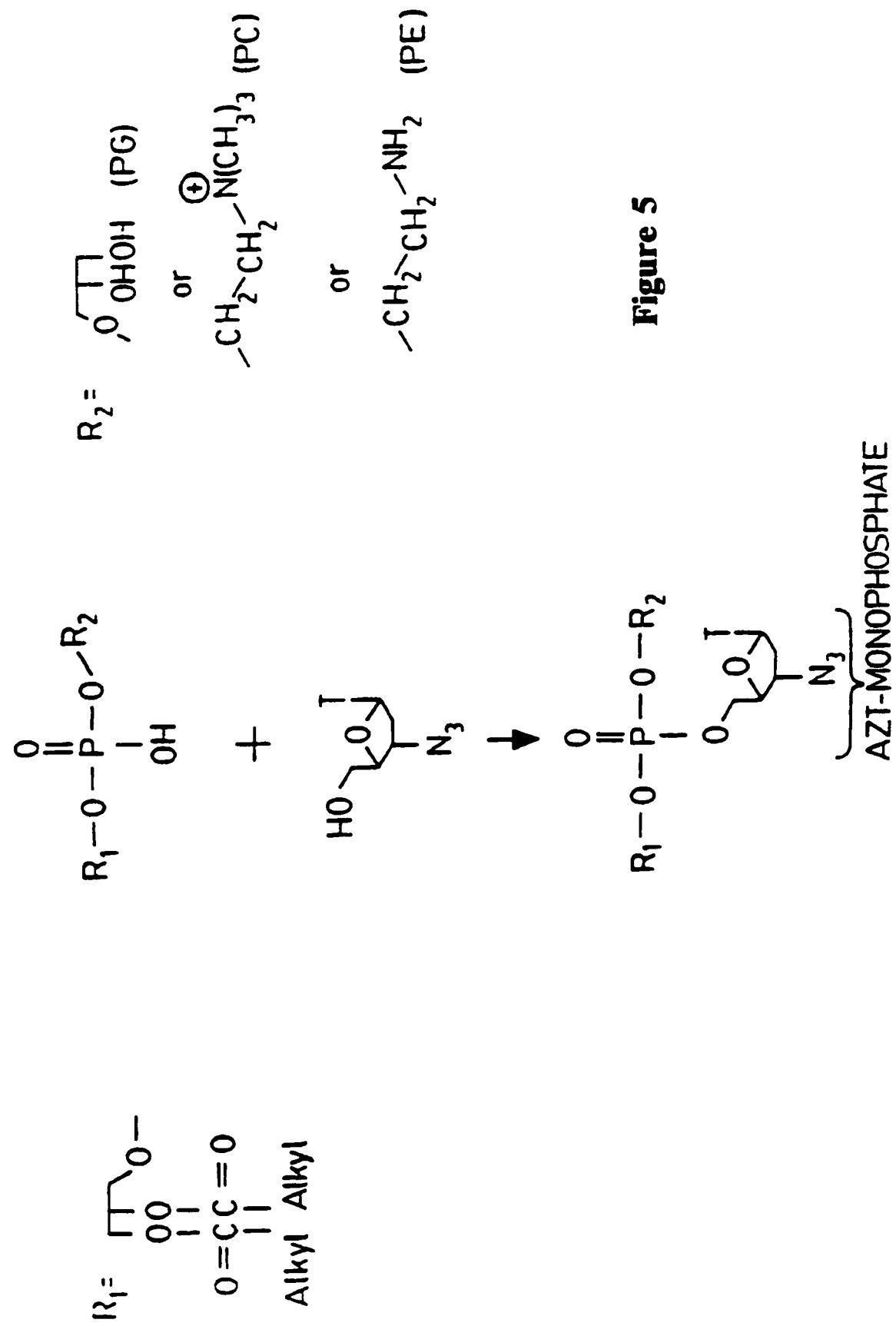
FIG. 5 depicts the synthetic scheme put forth in Example 5.
Figure 6:
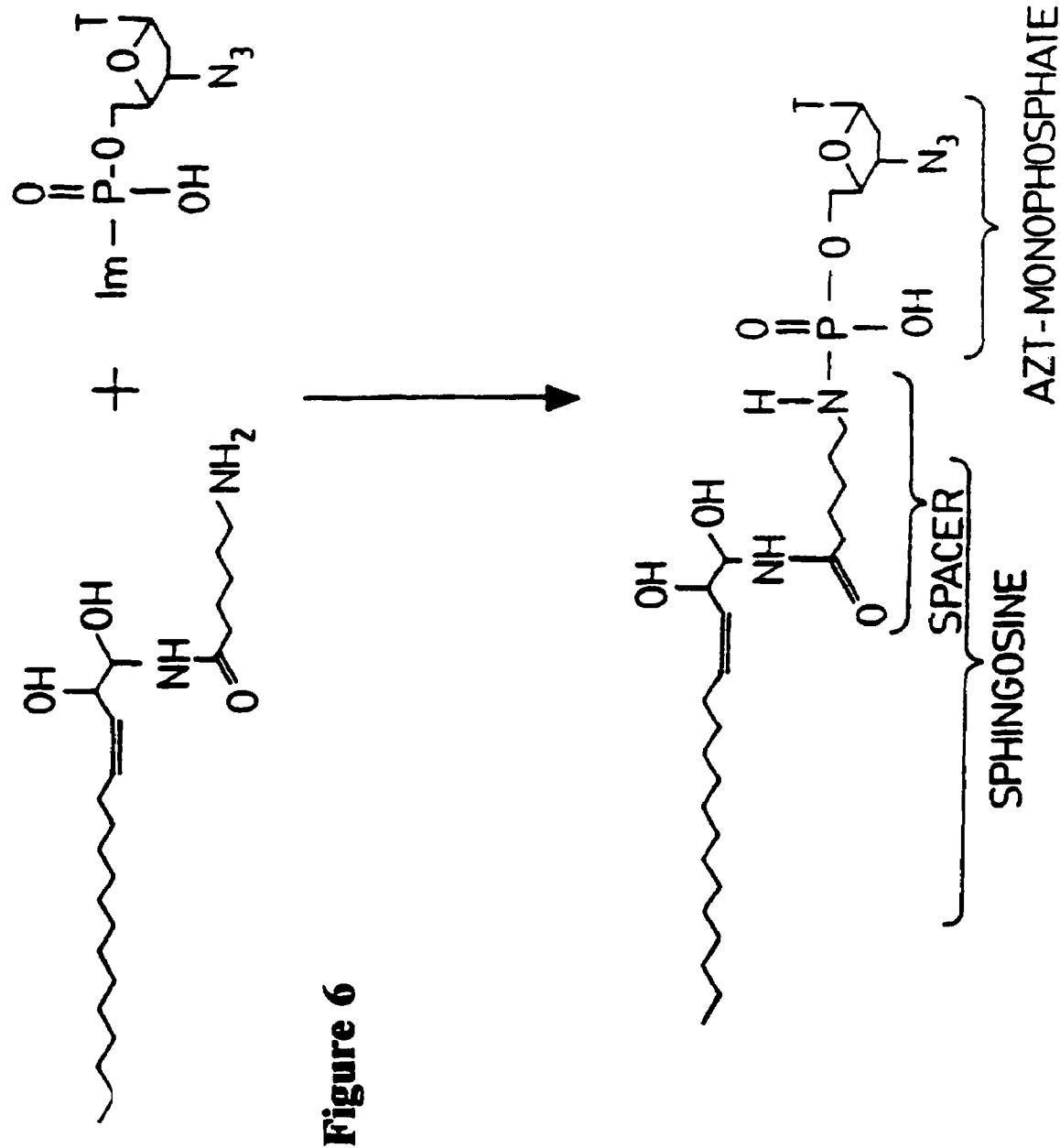
FIG. 6 depicts the synthetic scheme put forth in Example 6.
Figure 7:
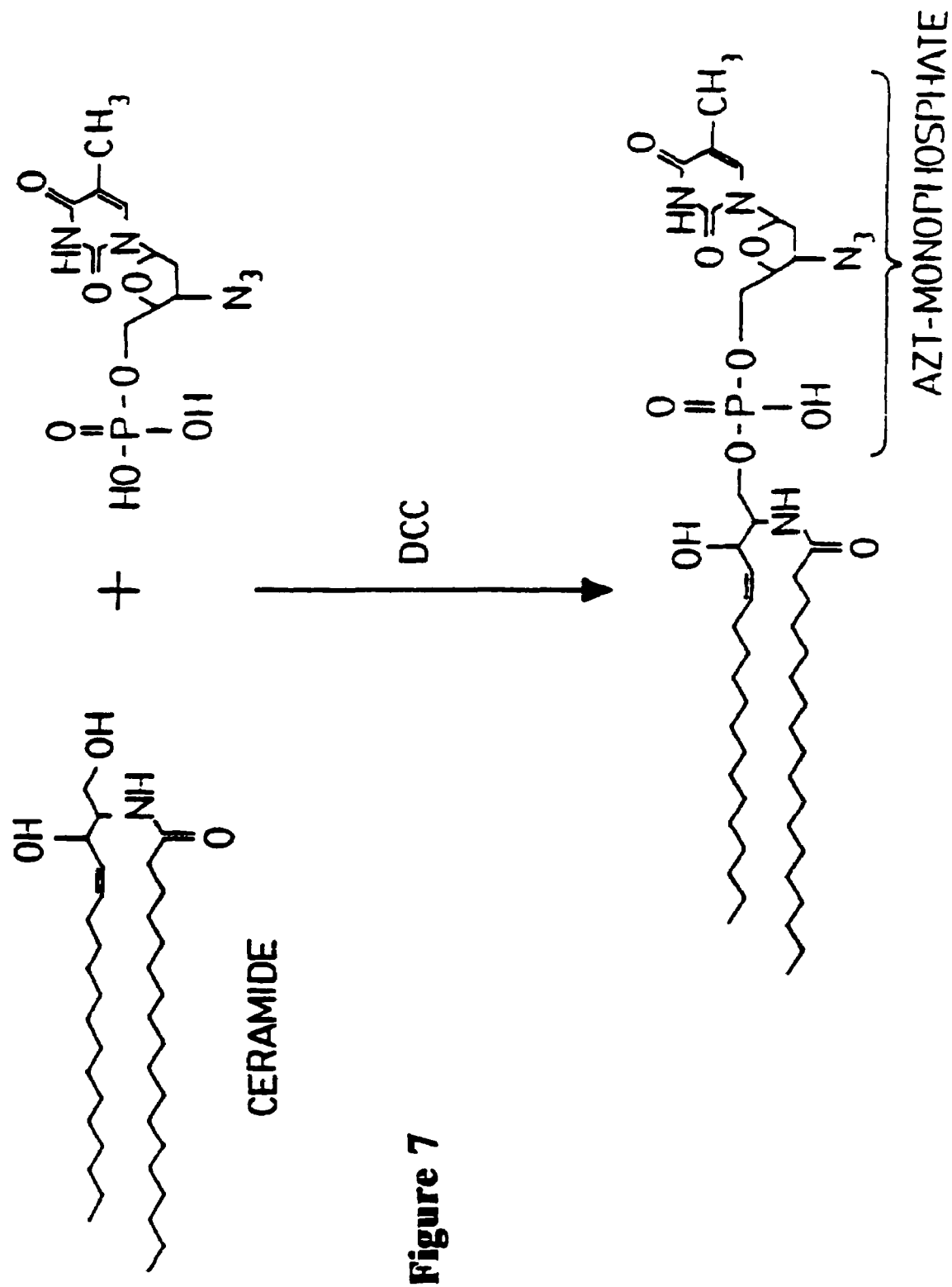
FIG. 7 depicts the synthetic scheme put forth in Example 7.

The present invention provides compositions of matter and methods for facilitating the entry biologically-active compounds into phagocytic cells. For the purposes of this invention, the term "biologically-active compound" is intended to encompass all naturally-occurring or synthetic compounds capable of eliciting a biological response or having an effect, either beneficial or cytotoxic, on biological systems, particularly cells and cellular organelles. These compounds are intended to include but are not limited to all varieties of drugs, particularly antimicrobial drugs, defined herein to include antiviral, antibacterial, fungicidal and anti-protozoal, especially anti-plasmodial drugs, as well as peptides including antimicrobial peptides. Also included in the definition of "biologically active compounds" are antineoplastic drugs, particularly methotrexate and 5-fluorouracil and other antineoplastic drugs.

This invention provides microparticle-linked antiviral and antimicrobial agents for specific cell targeting to phagocytic mammalian cells. As used herein, phagocytic mammalian cells include but are not limited to monocytes, macrophages, alveolar macrophages, peritoneal macrophages, Kuppfer cells of the liver, macrophage cells resident in the central nervous system and the skin, all tissue inflammatory and noninflammatory macrophages, and phagocytic bone marrow cells.

This invention provides microparticle-linked antimicrobial agents wherein an antiviral or antimicrobial drug is linked to a microparticle via a cleavable linker moiety. The term "antimicrobial drug" is intended to encompass any pharmacological agent effective in inhibiting, attenuating, combating or overcoming infection of phagocytic mammalian cells by a microbial pathogen in vivo or in vitro. Antimicrobial drugs as provided as components of the antimicrobial agents of the invention include but are not limited to penicillin and drugs of the penicillin family of antimicrobial drugs, including but not limited to penicillin-G, penicillin-V, phenethicillin, ampicillin, amoxacillin, cyclacillin, bacampicillin, hetacillin, cloxacillin, dicloxacillin, methicillin, nafcillin, oxacillin, azlocillin, carbenicillin, mezlocillin, piperacillin, ticaricillin, and imipenim; cephalosporin and drugs of the cephalosporin family, including but not limited to cefadroxil, cefazolin, caphalexn, cephalothin, cephapirin, cephradine, cefaclor, cefamandole, cefonicid, cefoxin, cefuroxime, ceforamide, cefotetan, cefinetazole, cefoperazone, cefotaxime, ceftizoxime, ceftizone, moxalactam, ceftazidime, and cefixime; aminoglycoside drugs and drugs of the aminoglycoside family, including but not limited to streptomycin, neomycin, kanamycin, gentamycin, tobramycin, amikacin, and netilmicin; macrolide and drugs of the macrolide family, exemplified by azithromycin, clarithromycin, roxithromycin, erythromycin, lincomycin, and clindamycin; tetracyclin and drugs of the tetracyclin family, for example, tetracyclin, oxytetracyclin, democlocyclin, methacyclin, doxycyclin, and minocyclin; quinoline and quinoline-like drugs, such as, for example, naladixic acid, cinoxacin, norfloxacin, ciprofloxacin, ofloxicin, enoxacin, and pefloxacin; antimicrobial peptides, including but not limited to polymixin B, colistin, and bacatracin, as well as other antimicrobial peptides such as defensins (Lehrer et al., 1991, *Cell* 64: 229-230), magainins (Zasloff, 1987, *Proc. Natl. Acad. Sci. USA* 84: 5449-5453), cecropins (Lee et al., 1989, *Proc. Natl. Acad. Sci. USA* 86: 9159-9162 and Boman et al., 1990, *Eur. J. Biochem.* 201: 23-31), and others, provided as naturally-occurring or as the result of engineering to make such peptides resistant to the action of pathogen-specific proteases and other deactivating enzymes; other antimicrobial drugs, including chloramphenicol, vancomycin, rifampicin, metronidazole, ethambutol, pyrazinamide, sulfonamides, isoniazid, and erythromycin. Antiviral drugs, including but not limited to acyclovir, gangcyclovir, azidothymidine, cytidine arabinoside, ribavirin, amantadine, iododeoxyuridine, poscarnet, and trifluridine are also encompassed by this definition and are expressly included therein.

The invention also provides microparticle-linked antimicrobial agents wherein an antimicrobial agent is a toxin capable of specific cytotoxicity against the microbe, its host cell or both. The term "toxin" is intended to encompass any pharmacological agent capable of such toxicity, including for example ricin from jack bean, diphtheria toxin, and other naturally-occurring and man-made toxins.

In the antimicrobial agents as provided by this invention, said antimicrobial drugs are linked to microparticles that are specifically phagocytized by phagocytic mammalian cells. It is an advantage of the present invention that antiviral and antimicrobial drugs are specifically targeted to phagocytic mammalian cells, including, inter alia, monocytes and macrophages as provided further below, by attachment to the microparticles that are a component of the antimicrobial agents of the invention. The term "microparticle" as used herein is intended to encompass any particulate bead, sphere, particle or carrier, whether biodegradable or nonbiodegradable, comprised of naturally-occurring or synthetic, organic or inorganic materials, that is specifically phagocytized by phagocytic mammalian cells.

In one embodiment of the antiviral and antimicrobial agents of the invention, said microparticle is a porous particle having a defined degree of porosity and comprised of pores having a defined size range, wherein the antiviral or antimicrobial drugs are impregnated within the pores of the microparticle. In such embodiments, a chemically or enzymatically-degradable coating covers the surface or outside extent of the microparticle, wherein the coating is non-specifically degraded, chemically or enzymatically, within a phagocytic cell after phagocytosis.

In a second embodiment of the invention, the microparticle is either a porous or a nonporous particle. In such embodiments, the surface or outside extent of the microparticle comprises chemically functional groups that form covalent linkages with the antiviral or antimicrobial drug component of the antimicrobial agents of the invention, preferably via a chemically or enzymatically cleavable linker moiety. In such embodiments, the cleavable linked moiety is non-specifically chemically or enzymatically cleaved within a phagocytic cell after phagocytosis.

In a third embodiment of the invention, the microparticle is nonporous and the antiviral or antimicrobial drug is coated on the outside of the microparticle, the microparticle further coated with a coating material to control release of the antiviral or antimicrobial drug in a phagocytic cell. In such embodiments, a chemically or enzymatically-degradable coating covers the surface or outside extent of the microparticle, wherein the coating is non-specifically degraded, chemically or enzymatically, within a phagocytic cell after phagocytosis.

The microparticle component of the antiviral or antimicrobial agents of the invention include any particulate bead, sphere, particle or carrier having a diameter of about 1 to about 1000 nanometers (about 0.001-1 µm). The microparticles of the invention are provided comprised of polystyrene, cellulose, silica, and various polysaccharides including dextran, agarose, cellulose and modified, crosslinked and derivatized embodiments thereof. Specific examples of the microparticles of the invention include polystyrene, cellulose, dextran crosslinked with epichlorohydrin (Sephadex™, Pharmacia, Uppsala, Sweden), polyacrylamide crosslinked with bisacrylamide (Biogel™, BioRad, USA), agar, glass beads and latex beads. Derivatized microparticles include microparticles derivatized with carboxyalkyl groups such as carboxymethyl, phosphoryl and substituted phosphoryl groups, sulfate, sulfhydryl and sulfonyl groups, and amino and substituted amino groups.

In the antimicrobial agents of the invention as provided in one aspect, the microparticles and antiviral and antimicrobial drugs are linked via a chemically or enzymatically cleavable linker moiety. In another aspect of the antimicrobial agents of the invention, the antiviral and antimicrobial drugs are impregnated within porous microparticles coated with a chemically or enzymatically degradable coating. In another aspect of the antimicrobial agents of the invention, antiviral or antimicrobial drugs coat the external surface of a nonporous microparticle, which is thereafter further coated with a chemically or enzymatically degradable coating. In all aspects, release of the antiviral or antimicrobial drug is dependent on specific chemical or enzymatic cleavage of the coating or linker moieties inside phagocytic cells after phagocytosis of the antimicrobial agent.

In certain embodiments, the antimicrobial agents of the invention also comprise polar lipids which are chemically conjugated with the biologically-active compounds of the invention via a specific linker moiety. As provided by the invention, the biologically active compound has a biological activity that is reduced, suppressed, inhibited or ablated by formation of the polar lipid conjugate, and that is improved, restored or activated upon chemical or enzymatic cleavage of the specific linker moiety and liberation of the biologically active compound from the polar lipid conjugate. Alternatively, the invention provides the biologically active compound in an inactive form such as a prodrug, that is specifically activated inside a phagocytic cell infected with a microorganism, preferably a pathological or disease-causing microorganism.

Liberation of the biologically active compound from the polar lipid conjugate, or activation of the inactive prodrug, is specifically achieved inside a phagocytic cell infected with a microorganism, preferably a pathological or disease-causing microorganism, by preparing the antimicrobial agents of the invention wherein the specific linker moiety or the prodrug activation is mediated by chemical reaction under physiological conditions specific for infection of a phagocytic mammalian cell with a particular microorganism, most preferably a pathological or disease-causing microorganism. In this embodiment, specific cleavage is due to an chemical linkage which is labile within the infected phagocytic cell due to conditions caused by or that result from infection of the phagocytic cell with a particular microbial pathogen. Alternatively, the specific linker moiety or the prodrug activation is mediated by enzyme action of an enzyme produced by (i.e., encoded by the microorganism) or induced by (i.e., encoded by the host phagocytic cell) infection of a phagocytic mammalian cell with a particular microorganism, most preferably a pathological or disease-causing microorganism.

Examples of such combinations resulting in specific release of the antiviral or antimicrobial drug component of the antimicrobial agents of the invention within infected phagocytic cells include but are not limited to a urea-based linker for use against a pathogen which produces urease (e.g., *Mycobacteria* spp. and *B. pertussis*); a peptide linker comprised of (AlaAlaAlaAla SEQ ID NO:1)n, wherein n can be an integer from 1-5, for use against a pathogen that produces the protease oligopeptidase A (e.g., *Salmonella* spp.); a peptide comprised of from 3 to about 20 amino acids comprising the sequence --Pro-Xaa-Pro--, where Xaa is any amino acid, for use against a pathogen that produced proline peptidase (e.g., *Salmonella* spp.); peptides comprising the dipeptide MetMet or LeuAla, or peptides comprising the amino acid sequence GSHLVEAL (SEQ ID NO:2), HLVRALYL (SEQ ID NO:3), VEALYLVC (SEQ ID NO:4), or EALYLVCG (SEQ ID NO:5), for use against human immunodeficiency virus 1 producing a specific protease termed HIV-1 protease; a peptide comprising the amino acid sequence: -Ala-Xaa-CysAcm-Tyr-Cys-Arg-Ile-Pro-Ala-CysAcm-Ile-Ala-Gly-Asp-Arg-Arg-Tyr-Gly-Thr-CysAcm-Ile-Tyr-Gln-Gly-Arg-Leu-Trp-Ala-Phe-CysAcm-CysAcm- (SEQ ID NO:6), wherein the microbial pathogen expresses an enzymatic activity that specifically disables the endogenous antimicrobial peptide defensin (e.g., *Mycobacterium* spp. and *L. pneumophila*), (-CysAcm-) represent cysteine residues having the sidechain sulfur atom protected by covalent linkage to an acetamidomethyl group (it will be recognized that embodiments of such peptides having alternative sulfur protecting groups are also within the scope of the disclosure herein) and Xaa is either absent or Asp; said peptides are also useful as components of the microparticulate antimicrobial compounds of the invention against a pathogen such as *Legionella* spp. producing a 39 kDa metalloprotease; hippurate esters that are hydrolyzed by pathogen-specific (e.g., *L. pneumophila* and *Listeria* spp.) hydrolase; nicotinic acid amides cleaved by nicotinamidases, pyrazinamides cleaved by pyrazinamidase; allolactose linkages cleaved by galactosidase; and allantoate linkages cleaved by allantoicase (e.g., *Mycobacterium* spp.).

In certain specific embodiments, combinations or mixtures of the antimicrobial agents of the invention will comprise the therapeutic pharmaceutical agents of the invention, as provided below. In other embodiments, said mixtures will include compositions of matter comprising a microparticle covalently linked to an enzyme having an activity that recognizes and cleaves the cleavable linker or coating moiety of the other antimicrobial agent component of the mixture, said enzyme-linked microparticles having activity as drug release accelerators. In preferred embodiments, the activity or optimal activity of such enzymatic drug release accelerators will be achieved only inside a phagocytic mammalian cell, for example, in a phagolysosome.

The cleavable linker or coating material comprising the microparticles of the invention is non-specifically degraded inside a phagocytic cell that has phagocytized the microparticles. Thus, encompassed within the cleavable linkers and coating materials of the microparticles of the invention are materials that are chemically or enzymatically degraded in a phagocytic cell using the cellular machinery, enzymes and pathways for degradation and processing of phagocytized materials. Examples of the types of cellular enzymes explicitly recited as being within the scope of this invention are arylsulfatases, most preferably lysosomal arylsulfatases, as described in Lukatela et al. (1998, *Biochemistry* 37: 3654-3664) and Recksiek et al. (1998, *J. Biol. Chem.* 273 6096-6103). For example, microparticles coated with polymers comprising linear sulfate esters (such as peptides linked tail-to-tail via a sulfate ester linkage to the carboxyl termini of the peptides) are appropriate substrates for arylsulfatases. In another example, chondroitin sulfate coatings are expected to be non-specifically degraded by lysosomal arylsulfatases. Acid proteases (as described ion Aniento et al., 1997, *Electrophoresis* 18: 2638-2644) are another class of cellular enzymes, substrates of which can be used in the cleavable linkers and coating materials of the invention. In this embodiment, peptides comprising the sequence $(Asp)_n(Glu)_m$, $(Glu)_n$, or $(Asp-Glu)_n$, where $2<n<\sim50$ and $m>1$ can be used as the cleavable linkers and coating materials (most preferably wherein long homopolymeric Asp sequences are avoided) and be non-specifically cleaved in a phagocytic cell. Alternatively, substrates for lipases, such as cholesterol-fatty acid esters (as described in Du et al., 1998, *Gene* 208: 285-295) can be used for to comprise the cleavable linkers or coating materials of the microparticles of the invention.

For the purposes of this invention, the term "non-specific" when used with regard to the cleavable linkers or coating materials is intended to indicate that cleavage is not specific for phagocytic cells infected with a microorganism, but that the cleavable linker moieties and coating materials are expected to be cleaved in any phagocytic cell. The particular mechanisms of cleavage, particularly wherein said mechanisms involve enzymatic cleavage, will be characterized by the conventionally-recognized specificity between enzyme and substrate.

In other embodiments, a multiplicity of biologically-active compounds comprise the microparticle embodiments of the invention.

In specific embodiments of the antimicrobial agents of the invention, said antimicrobial agents are conjugated with a polar lipid targeting moiety comprised of one or a plurality of polar lipid molecules. The polar lipid moiety in such embodiments is covalently linked to either the antiviral or antimicrobial drug via a specific linker moiety as described herein. The polar lipid moiety is linked to the antiviral or antimicrobial drug through an specific linker moiety comprising a first functional linker group and a second functional linker group. The term "polar lipid moiety" as defined herein is intended to mean any polar lipid having an affinity for, or capable of crossing, a biological membrane. Polar lipid moieties comprising said embodiments of the invention include but are not limited to acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin, phosphatidic acid, sphingomyelin and other sphingolipids, as these terms are understood in the art (see, Lehninger, *Biochemistry*, 2d ed., Chapters 11 & 24, Worth Publishers: New York, 1975).

These embodiments of the invention may be further comprised of an specific linker moiety comprising a first end and a second end, each end of the linker having a functional linking group. For the purposes of this invention, the term "specific linker" or "specific linker moiety" is intended to encompass any chemical entity that links a biologically-active compound such as an antiviral or antimicrobial drug and a polar lipid moiety, and having a specificity for a chemical or enzymatic reaction capable of cleaving the specific linker moiety only within a phagocytic cell, preferably a phagocytic mammalian cell, infected with a particular microorganism, most preferably a pathological or disease-causing microorganism. Such specific linker moieties are designed to facilitate, control, modulate and regulate the release of the biologically-active compound at a desired intracellular target site. Such specific linkers also facilitate enzymatic release at certain intracellular sites.

As used herein, the term "linker functional group" is defined as any functional group for covalently linking the polar lipid moiety or biologically-active agent to the specific linker moiety. This definition also includes functional groups comprising a biologically active compound, the polar lipid, a microparticle or any appropriate combination thereof.

Linker functional groups can be designated either "weak" or "strong" based on the stability of the covalent bond which the linker functional group will form. The weak functionalities include, but are not limited to phosphoramide, phosphoester, carbonate, amide, carboxyl-phosphoryl anhydride, ester and thioester. The strong functionalities include, but are not limited to ether, thioether, amine, amide and ester. Strong linker functional groups comprise the functional covalent linkages between the biologically active compounds, the specific linker moieties and the polar lipids of the conjugates of the invention, wherein the conjugates are chemically stable inside phagocytic cells and are cleaved only under specific conditions, i.e., infection of the host cell by a particular microorganism. Enzyme-mediated modes of release will not necessarily be correlated with bond strength in such embodiments of the invention; however, strong linkages are intended to minimize inappropriate release of the biologically active compounds of the conjugates of the invention in cells not infected with a microorganism. Specific linker moieties comprising enzyme active site recognition groups, such as linker groups comprising peptides having proteolytic cleavage sites therein, are but one example of the types of specific linker moieties within the scope of the present invention.

The antimicrobial agents of this invention are useful in inhibiting, attenuating, arresting, combating and overcoming infection of phagocytic mammalian cells with pathogenic microorganisms in vivo and in vitro. To this end, the antimicrobial agents of the invention are administered to an animal infected with a pathogenic microorganism acutely or chronically infecting phagocytic mammalian cells. The antimicrobial agents of the invention for this use are administered in a dosage and using a therapeutic protocol sufficient to have an antimicrobial effect in the phagocytic cells of the animal. Thus, methods of treating microbial infections in a mammal, specifically infections of phagocytic mammalian cells, are provided. Pharmaceutical compositions useful in the methods provided by the invention are also provided.

The following Examples illustrate certain aspects of the above-described method and advantageous results. The following examples are shown by way of illustration and not by way of limitation.

EXAMPLE 1

An inactive, prodrug form of an antimicrobial agent is prepared by conjugating a non-specifically cleavable peptide (i.e., one that will be cleaved in a phagocytic cell) to a derivatized microparticle as follows. An derivatized microparticle comprising unconjugated amino groups is reacted with a proteolytically-inert peptide in which the terminal amine and any of the constituent amino acid sidechain reactive amines are covered by tert-butoxycarbonyl (t-Boc) protecting groups in the presence of triphenyl phosphine as described by Kishimoto (1975, *Chem. Phys. Lipids* 15: 33-36). The peptide/microparticle conjugate is then reacted in the presence of pyridine hydrofluoride as described by Matsuura et al. (1976, *J. Chem. Soc. Chem. Comm.* xx: 451459) to remove the t-Boc protecting groups. The peptide/microparticle is then conjugated to the non-specifically cleavable peptide, in which the terminal amine and any of the constituent amino acid sidechain reactive amines are covered by t-Boc protecting groups, as described in the presence of triphenyl phosphine. After deprotection of reactive amines with pyridine hydrofluoride as described, an inactive, prodrug form of an antimicrobial drug having a reactive carboxylic acid group is conjugated to a free amino group of the microparticle/peptide/specifically-cleavable peptide to yield the antimicrobial agent of the invention. This reaction scheme is illustrated in FIG. 1.

EXAMPLE 2

An antiviral compound (HIV1 protease inhibitor; compound 8) is conjugated to sphingosine as follows. Sphingosine is reacted with 1,3 bis(trimethylsilyl)urea as described by Verbloom et al. (1981, *Synthesis* 1032: 807-809) to give a trimethylsilyl derivative of sphingosine. The sphingosine derivative is then conjugated with the antigenically-active peptide in which the terminal amine and any of the constituent amino acid sidechain reactive amines are covered by tert-butoxycarbonyl (t-Boc) protecting groups in the presence of diethylazo-dicarboxylate (DEAD) and triphenyl phosphine as described by Kishimoto (1975, *Chem. Phys. Lipids* 15: 33-36). The sphingosine/peptide conjugate is then reacted in the presence of pyridine hydrofluoride as described by Matsuura et al. (1976, *J. Chem. Soc. Chem. Comm*. xx: 451-459) to remove the t-Boc protecting group, to yield the antigenically-active peptide covalently linked to sphingosine through an amide bond. This reaction scheme is illustrated in FIG. 2. Sphingosine/drug conjugates are then linked to microparticles as described in Example 1.

EXAMPLE 3

An antiviral compound (compound 8) is conjugated to ceramide via a polyglycine linker as follows and as illustrated in FIG. 3. The amino terminus of polyglycine is protected by a t-Boc group. Polyglycine is conjugated through its carboxy terminus to ceramide forming an ester linkage, as described in Anderson et al., ibid. The resulting compound is then conjugated through the amino terminus of the polyglycine residue. The amino terminus of Compound 8 is also protected by a t-Boc protecting group. Conjugation with polyglycyl-sphingosine takes place between the amino terminus of the polyglycyl linker moiety and the carboxy terminus of the HIV-1 protease inhibitor. This reaction is carried out in the presence of DEAD and triphenyl phosphine as described in Examples 1 and 2. Following this conjugation, the amino terminus of the HIV-1 protease inhibitor residue is deprotected according to the method of Matsuura et al., ibid. Ceramide/drug conjugates are then linked to microparticles as described in Example 1, or used to impregnate a porous microparticle, or used to coat a non-porous microparticle.

EXAMPLE 4

An antiviral compound is prepared wherein ceramide is first conjugated to a first end of an oligomeric 3-hydroxy propanoic acid linker through an ester functional group, and wherein AZT is conjugated to a second end of said polyester linker through a phosphodiester bond. First a polyester linker is obtained, having a carboxyl at a first end and a triphenylmethyl group esterified to a second end. This linker is conjugated to ceramide at its first end through an ester functional linker group according to the method of Anderson et al., ibid. This compound is then conjugated through the second end of the linker compound to AZT monophosphate by means of a phosphodiester bond according to the method of Baer (1955, *Can. J. Biochem. Phys*. 34: 288). In this antiviral compound, the bond breakage between the linker and the drug would be slow in the absence of a phosphohydrolase. This reaction scheme is illustrated in FIG. 4. Ceramide/drug conjugates are then linked to microparticles as described in Example, 1, or used to impregnate a porous microparticle, or used to coat a non-porous microparticle.

EXAMPLE 5

An antiviral compound wherein phosphatidic acid, phosphatidyl choline, phosphatidyl serine, phosphatidyl inositol, phosphatidyl glycerol or phosphatidylethanolamine is linked through a phosphoester linker functional group to the antiviral drug azidothymidine (AZT). Phosphatidic acid, phosphatidyl choline, phosphatidyl serine, phosphatidyl inositol, phosphatidyl glycerol or phosphatidyl ethanolamine is conjugated to AZT according to the method of Salord et al. (1986, *Biochim. Biophys. Acta* 886: 64-75). This reaction scheme is illustrated in FIG. 5. Phospholipid/drug conjugates are then linked to microparticles as described in Example 1, or used to impregnate a porous microparticle, or used to coat a non-porous microparticle.

EXAMPLE 6

An antiviral compound is prepared wherein aminohexanoyl sphingosine is conjugated to AZT. Aminohexanoyl sphingosine is conjugated with AZT according to the method of Kishimoto (1975, *Chem. Phys. Lipid* 15: 33-36). This reaction scheme is illustrated in FIG. 6 to yield aminohexanoyl sphingosine conjugated to AZT through a phosphoramide bond. Such conjugates are then linked to microparticles as described in Example 1, or used to impregnate a porous microparticle, or used to coat a non-porous microparticle.

EXAMPLE 7

An antiviral compound consisting of ceramide conjugated to AZT-monophosphate is provided. Ceramide is reacted with AZT-monophosphate in the presence of dicyclohexylcarbodiimide as described in Smith and Khorana (1958, *J. Amer. Chem. Soc*. 80: 1141) to yield ceramide conjugated through a phosphodiester bond to AZT-monophosphate. This reaction scheme is illustrated in FIG. 7. The AZT/polar lipid conjugate is then linked to microparticles as described in Example 1, or used to impregnate a porous microparticle, or used to coat a non-porous microparticle.

EXAMPLE 8

Figure 8:
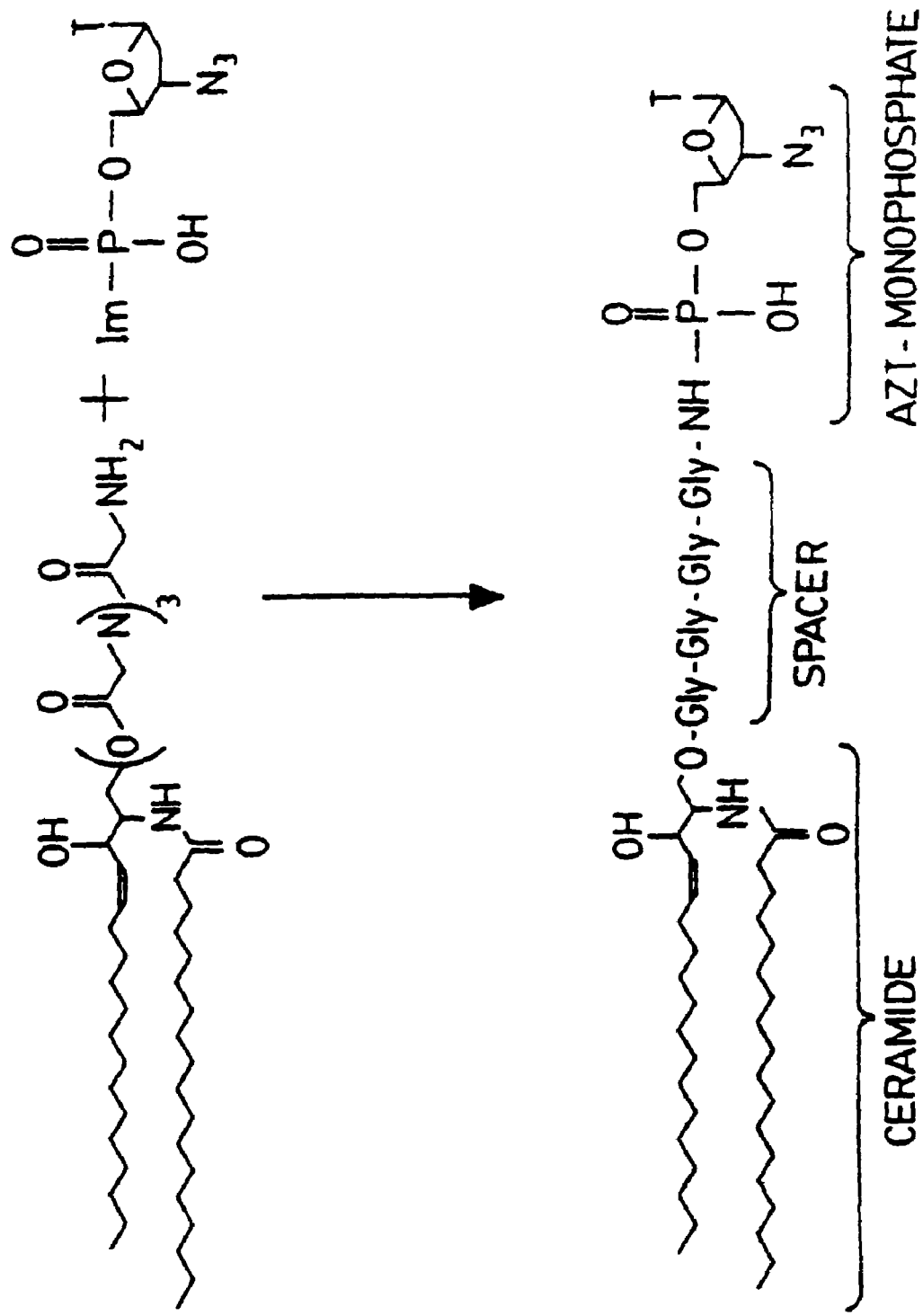
FIG. 8 depicts the synthetic scheme put forth in Example 8.

An antiviral compound is prepared wherein ceramide is conjugated through an ester functional group to a first end of a polyglycine linker, and wherein AZT is conjugated through a phosphoester functional group to a second end of the polyglycine linker. Ceramide is first conjugated through an ester functional group to a first end of a polyglycine linker (as described in Example 2). The ceramide-polyglycine compound is then conjugated through a phosphoester bond to a second end of the polyglycine linker to AZT monophosphate according to the method of Paul and Anderson, ibid. This reaction scheme is illustrated in FIG. 8. Conjugates as prepared herein are then linked to microparticles as described in Example 1, or used to impregnate a porous microparticle, or used to coat a non-porous microparticle.

EXAMPLE 9

Figure 9A:
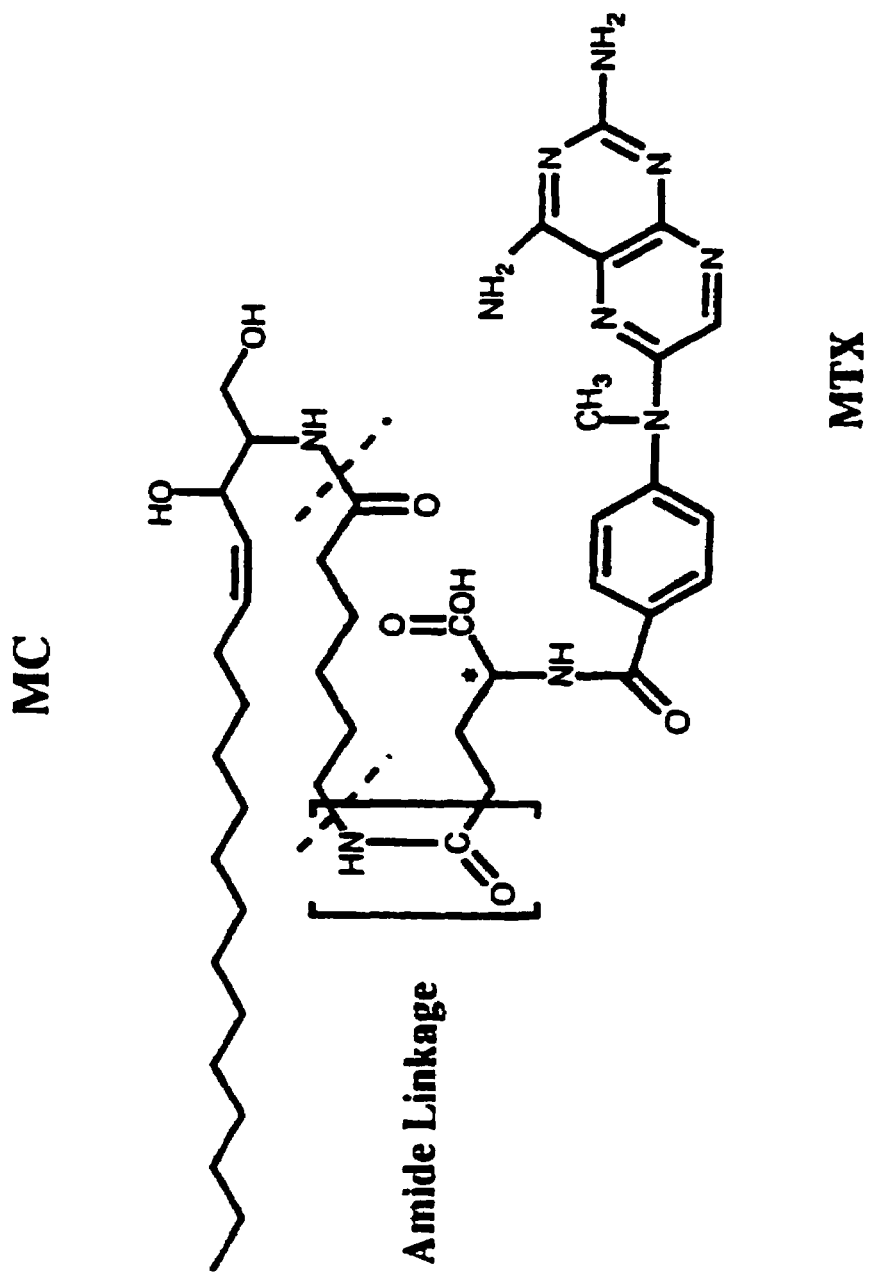
FIGS. 9A through 9D depict prodrugs tested as in Example 9.
Figure 9B:
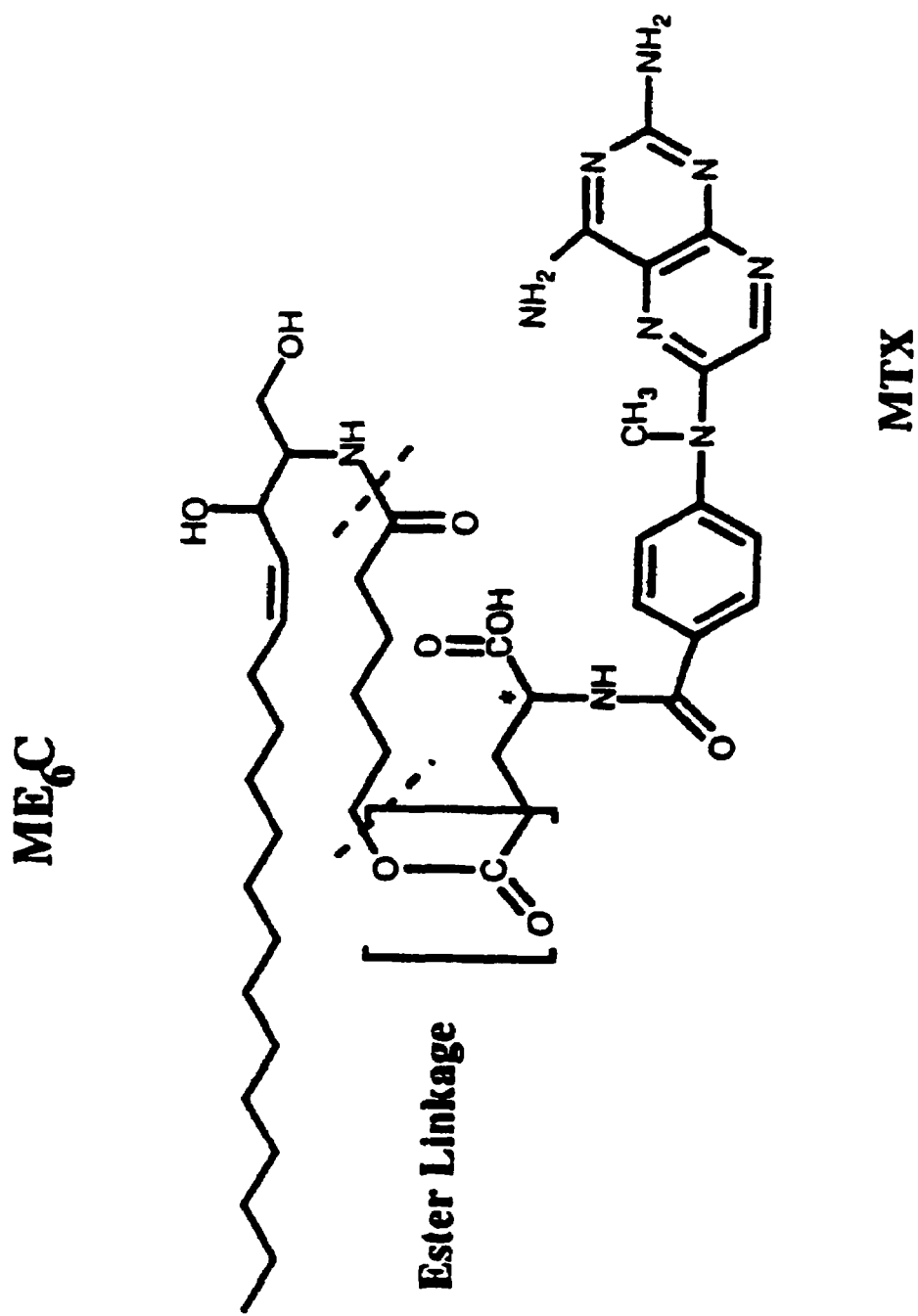
Figure 9C:
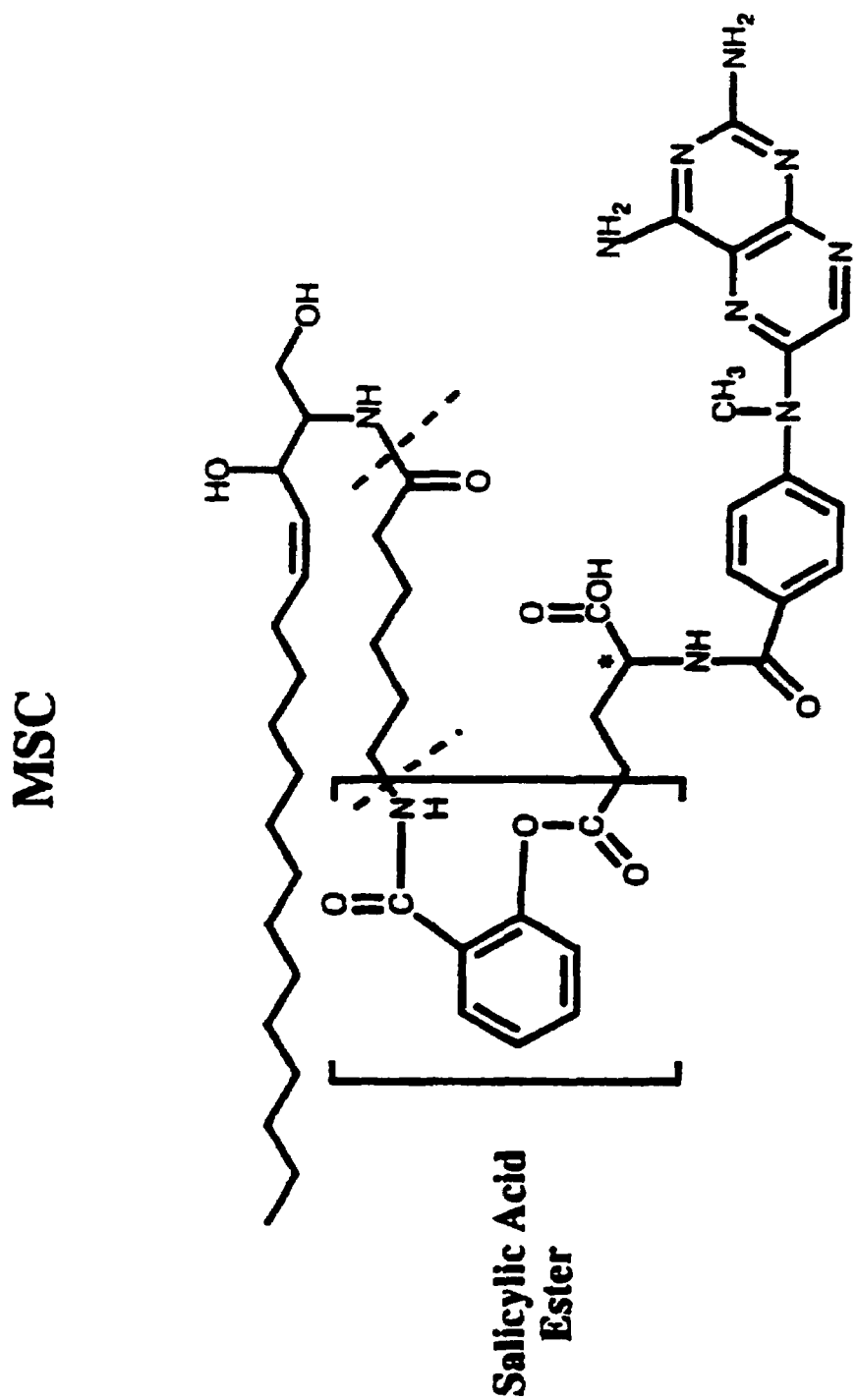
Figure 9D:
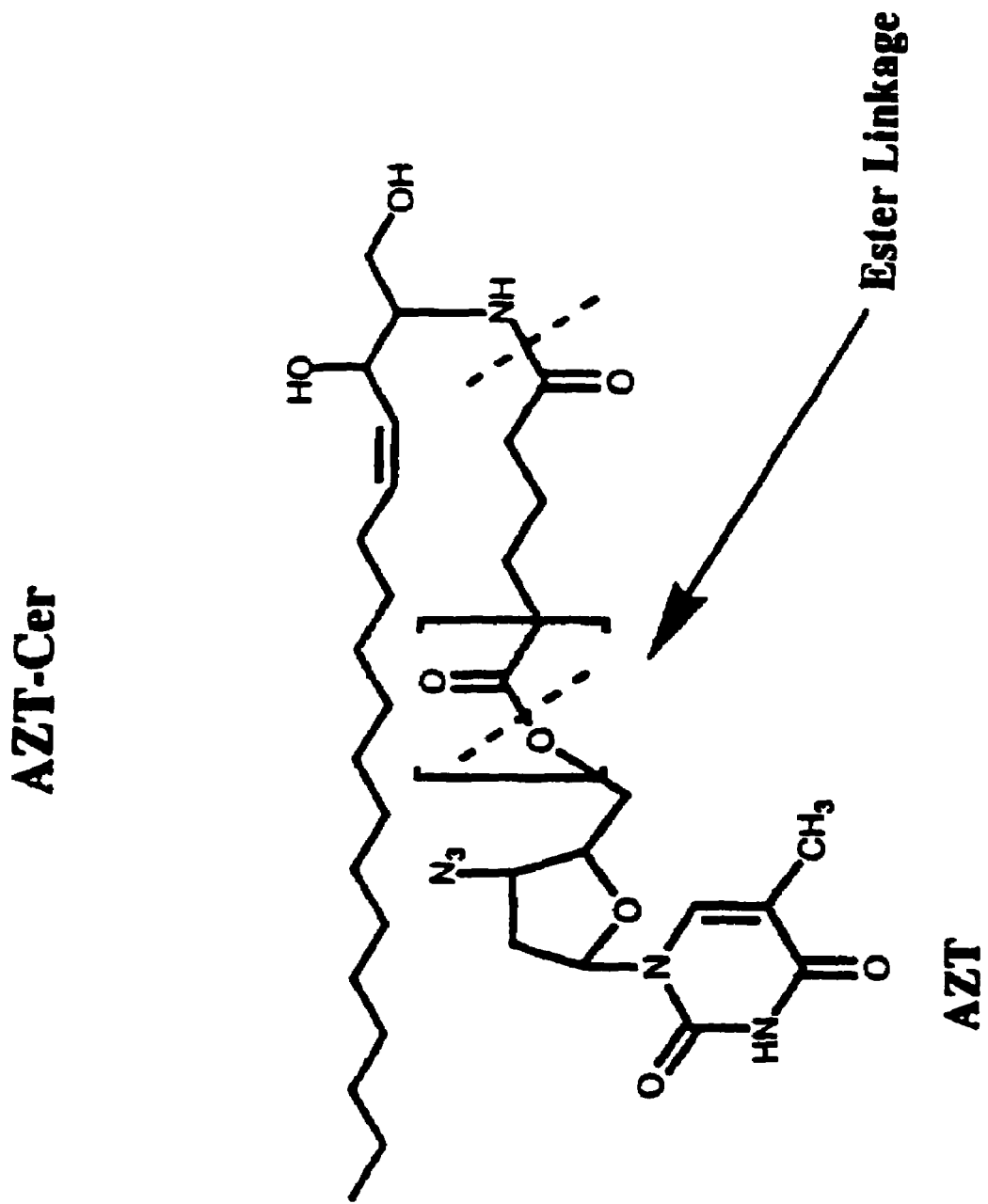

The effect of presenting a biologically active compound such as a drug to mammalian cells as a prodrug covalently linked to a polar lipid carrier moiety was determined as follows. The antifolate drug methotrexate was conjugated with a variety of polar lipid carriers via specific linker moieties having specific reactive functional groups. A representative sample of such compounds is shown in FIGS. 9A through 9C, wherein MC represents Mtx linked to sphingosine via an amide bond to a 6-aminohexanoic acid linker, $ME_6C$ represents. Mtx linked to sphingosine via an ester linkage to a 6-hydroxyhexanoic acid linker, and MSC represents Mtx linked to sphingosine via a salicylic acid ester linkage to a 6-aminohexanoic acid linker. Also studied was a conjugate of azidothymidine linked to sphingosine via an ester linkage to a 6-hydroxyhexanoic acid linker (N-AZT-ceramide). The compounds were tested for their growth inhibitory effects on murine NIH 3T3 cells growing in cell culture. About one million such cells per P100 tissue culture plate were grown in DMEM media supplemented with 10% fetal calf serum (GIBCO, Grand island, N.Y.) in the presence or absence of a growth-inhibitory equivalent of each prodrug. Cell numbers were determined after 70 hours growth in the presence or absence of the prodrug. In a second set of experiments was included in the growth media an amount of a brain homogenate containing an enzymatically-active esterase.

The results from these experiments are shown in Table I. As can be seen from these data, the MC prodrug had no effect on the growth and survival of the cells. This result did not change upon co-incubation with the esterase-containing brain extract, which was expected due to the nature of the drug/linker linkage (an amide bond). A different result was obtained with the $ME_6C$ conjugate. The prodrug was ineffective in inhibiting cell growth or survival in the absence of brain extract. Upon addition of the brain extract, a significant increase in Mtx cytotoxicity was observed. This is consistent with cleavage of the ester linkage by the brain extract-derived esterase. A similar result was obtained with the MCS conjugate, indicating that the brain extract esterase activity was capable of cleaving the salicylic acid ester.

Table II shows the results of drug uptake studies performed with the prodrug N-AZT-ceramide. Antiviral amounts of the prodrug conjugate were added to NIH 3T3 cell cultures, and the antiviral activity of the prodrug was found to be equivalent to the activity of free AZT. In addition, upon removal of the prodrug, intracellular retention of prodrug was found to be up to 15-fold higher than free AZT (Table II) over a 23 h period.

These results indicate that for Mtx-containing conjugates, the free drug must be released from the prodrug for biological activity. These results suggest that specific release of this drug, and perhaps others, can be achieved using cleavable linker moieties that are specifically cleaved only in pathogen-infected cells.

TABLE I

| Sample[1] | # cells/plate[2] | Sample[3] | # cells/plate[4] |
|---|---|---|---|
| Control/FBS | $7.8 \times 10^6$ | Control/FBS | $13 \times 10^6$ |
| $ME_6C$/FBS | $6.5 \times 10^6$ | MSC/FBS | $2.1 \times 10^6$ |
| $ME_6C$/brain | $2.7 \times 10^6$ | MSC/brain | $0.51 \times 10^6$ |
| Mtx/FBS | $0.16 \times 10^6$ | Mtx/FBS | $0.13 \times 10^6$ |
| Mtx/brain | $0.09 \times 10^6$ | Mtx/brain | $0.06 \times 10^6$ |
| Control/brain | N.D. | Control/brain | $6.2 \times 10^6$ |

[1] = cells incubated with drug/FBS or drug/brain extract for 1 hour at 37° C.
[2] = cell growth and survival determined 70 hours after drug addition
[3] = cells incubated with drug/FBS or drug/brain extract for 2 hours at 37° C.
[4] = cell growth and survival determined 72 hours after drug addition

| Time[1] | AZT[2] | N-AZT-Ceremide[2] |
|---|---|---|
| 0 hr. | 6.49 | 8.45 |
| 23 hr. | 0.55 | 7.78 |

[1] = time between the end of drug treatment and assay for intracellular drug concentration
[2] = $nM/10^6$ cells

EXAMPLE 10

Antimicrobial agents of the invention are used as follows. The antimicrobial agent or a negative control (saline) are administered to an animal infected with a microbial pathogen using both optimal and suboptimal dosages and the most appropriate route of administration. After an optimal time period (determined from the nature of the infection), phagocytic cells are collected from the animal and tested for infection with the microbial pathogen. Phagocytic cells from peripheral blood are isolated using conventional methods (Ficoll-Hypaque density gradient centrifugation) and tested for the presence of infectious microbial pathogens using conventional immunological, microbiological and biochemical testing protocols (see *Laboratory Test Handbook*, Jacobs et al., eds., Lexi-Comp, Inc: Cleveland, Ohio, 1994; *Clinical Laboratory Medicine*, McClatchey, ed., Williams & Wiklins: Baltimore, Md., 1994; *Clinical Diagnosis and Management by Laboratory*, 18th Ed., J. B. Henry, ed., W. B. Saunders: Philadelphia, 1991).

It should be understood that the foregoing disclosure emphasizes certain specific embodiments of the invention and that all modifications or alternatives equivalent thereto are within the spirit and scope of the invention as set forth in the appended claims.

We claim:

1. A composition of matter comprising a prodrug of a biologically-active compound, a nonporous microparticle, and an organic coating material, wherein the prodrug comprises a biologically active compound, a polar lipid moiety comprised of one or a plurality of polar lipid molecules and a specific linker moiety, wherein the specific linker moiety is covalently linked to both the biologically active compound and the polar lipid moiety, wherein the nonporous microparticle is first coated with the prodrug and said coated microparticle is further coated with the organic coating material, and wherein the organic coating material is nonspecifically degraded inside a phagocytic mammalian cell infected with a microorganism to allow release of the prodrug within the infected cell, and wherein the specific linker moiety is specifically cleaved in a phagocytic mammalian cell infected with a microorganism and the prodrug is specifically activated thereby, wherein the polar lipid is selected from the group consisting of acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid.

2. The composition of matter of claim 1, wherein the biologically-active compound is a peptide.

3. The composition of matter of claim 2, wherein the peptide is an antiviral peptide or an antimicrobial peptide.

4. The composition of matter of claim 1, wherein the prodrug is a prodrug of an antiviral drug or an antimicrobial drug.

5. The composition of matter of claim 1, wherein the biologically active compound is a toxin.

6. The composition of matter of claim 1, wherein the organic coating material is chemically degraded inside the mammalian phagocytic cell infected with a microorganism.

7. The composition of matter of claim 1, wherein the organic coating material is a substrate for a protein having an enzymatic activity, said protein being produced in the mammalian cell infected with a microorganism.

8. The composition of matter of claim 1, wherein the organic coating material is a substrate for a protein having enzymatic activity produced by the infected mammalian cell.

9. The composition of matter of claim 1, wherein the specific linker moiety is chemically cleaved inside the phagocytic mammalian cell.

10. The composition of matter of claim 1, wherein the coating material is chemically cleaved inside the phagocytic mammalian cell.

11. The composition of matter of claim 1, wherein the specific linker moiety is a peptide.

12. The composition of matter of claim 1, wherein the coating material, the specific linker moiety or both is a substrate for a protein having enzymatic activity produced by the mammalian cell.

13. The composition of matter of claim 2, wherein the peptide is a defensin peptide.

14. A pharmaceutical composition comprising the composition of matter of claim 1 in a pharmaceutically acceptable carrier.

15. A method of killing a virus or microorganism infecting a mammalian cell, the method comprising contacting said cell with the composition of claim 1, wherein the prodrug is a prodrug of an antiviral peptide or a prodrug of antimicrobial peptide.

16. A method of killing a virus or microorganism infecting a mammalian cell, the method comprising contacting said cell with the composition of claim 1, wherein the biologically active molecule compound is a toxin.

17. A method for treating a viral infection in a human wherein the infecting virus is present inside a phagocytic cell in the human, the method comprising administering a therapeutic effective amount of the composition of claim 1, to the human in a pharmaceutically acceptable carrier, wherein the prodrug is an antiviral peptide or antimicrobial peptide.

18. A method for treating a microbial or viral infection in a human wherein the infecting microbe or virus is present inside a phagocytic cell in the human, the method comprising administering a therapeutically effective amount of the composition of claim 1, to the human in a pharmaceutically acceptable carrier, wherein the prodrug is a toxin.

* * * * *

SEQUENCE LISTING

<160> NUMBER OF SEQ ID NOS: 6

<210> SEQ ID NO 1
<211> LENGTH: 4
<212> TYPE: PRT
<213> ORGANISM: Artificial
<220> FEATURE:
<223> OTHER INFORMATION: peptide linker

<400> SEQUENCE: 1

Ala Ala Ala Ala
1

<210> SEQ ID NO 2
<211> LENGTH: 8
<212> TYPE: PRT
<213> ORGANISM: Artificial
<220> FEATURE:
<223> OTHER INFORMATION: peptide linker

<400> SEQUENCE: 2

Gly Ser His Leu Val Glu Ala Leu
1               5

<210> SEQ ID NO 3
<211> LENGTH: 8
<212> TYPE: PRT
<213> ORGANISM: Artificial
<220> FEATURE:
<223> OTHER INFORMATION: peptide linker

<400> SEQUENCE: 3

His Leu Val Arg Ala Leu Tyr Leu
1               5

<210> SEQ ID NO 4
<211> LENGTH: 8
<212> TYPE: PRT
<213> ORGANISM: Artificial
<220> FEATURE:
<223> OTHER INFORMATION: peptide linker

<400> SEQUENCE: 4

Val Glu Ala Leu Tyr Leu Val Cys
1               5

<210> SEQ ID NO 5
<211> LENGTH: 8
<212> TYPE: PRT
<213> ORGANISM: Artificial
<220> FEATURE:
<223> OTHER INFORMATION: peptide linker

<400> SEQUENCE: 5

Glu Ala Leu Tyr Leu Val Cys Gly
1               5

<210> SEQ ID NO 6
<211> LENGTH: 31
<212> TYPE: PRT
<213> ORGANISM: Artificial
<220> FEATURE:
<223> OTHER INFORMATION: peptide linker
<220> FEATURE:
<221> NAME/KEY: MISC_FEATURE
<222> LOCATION: (2)..(2)

-continued

```
<223> OTHER INFORMATION: Xaa is absent or equals Asp

<400> SEQUENCE: 6

Ala Xaa Cys Tyr Cys Arg Ile Pro Ala Cys Ile Ala Gly Asp Arg Arg
1               5                   10                  15

Tyr Gly Thr Cys Ile Tyr Gln Gly Arg Leu Trp Ala Phe Cys Cys
            20                  25                  30
```